United States Patent [19]
Van Bavel et al.

[11] Patent Number: 5,337,604
[45] Date of Patent: Aug. 16, 1994

[54] APPARATUS FOR MEASURING SAP FLOW

[76] Inventors: Cornelius H. M. Van Bavel, Rte. 1, Box 923-9, Center Point, Tex. 78010; Michael G. Van Bavel, 1903 Woodvale Rd., Missouri City, Tex. 77489

[21] Appl. No.: 146,877

[22] Filed: Nov. 1, 1993

Related U.S. Application Data

[63] Continuation-in-part of Ser. No. 741,293, Aug. 6, 1991, Pat. No. 5,269,183.

[51] Int. Cl.$^5$ .............................................. G01F 1/68
[52] U.S. Cl. .................... 73/204.22; 73/204.24
[58] Field of Search ........... 73/204.16, 204.22, 204.24; 47/1.01

[56] References Cited
U.S. PATENT DOCUMENTS

| | | | |
|---|---|---|---|
| 4,384,578 | 5/1983 | Winkler | 73/204.22 |
| 4,745,805 | 5/1988 | Granier | 73/204.24 |
| 4,817,427 | 4/1989 | Kitano et al. | 73/204.16 |

FOREIGN PATENT DOCUMENTS 761973  1/1934  France ............................ 73/204.24

Primary Examiner—Herbert Goldstein
Attorney, Agent, or Firm—Harrison & Egbert

[57] ABSTRACT

A device for measuring sap flow in a stem region comprises a rigid housing, configured like a clam-shell, and insulated and sealed from intrusion from radiation or water or weather by a collar which circumscribes the housing situated around the stem region being measured. Enclosed within this housing is a substrate preferably constructed from a composite of foam tape and rubber gasket material to provide a means for the electronics to conform to a diversity of stem cross-sections and irregularities. Temperature-sensing electronics measure energy transferred from an internal heater strip to the ambient, to the stem region, and to measure heat flowing up the stem. Heat transfer related to sap flow in a stem region is determined from four signals, two signals provided by two pair of differential thermocouples, a signal generated from a thermopile, and a signal indicative of the millivoltage delivered to the heater.

18 Claims, 21 Drawing Sheets

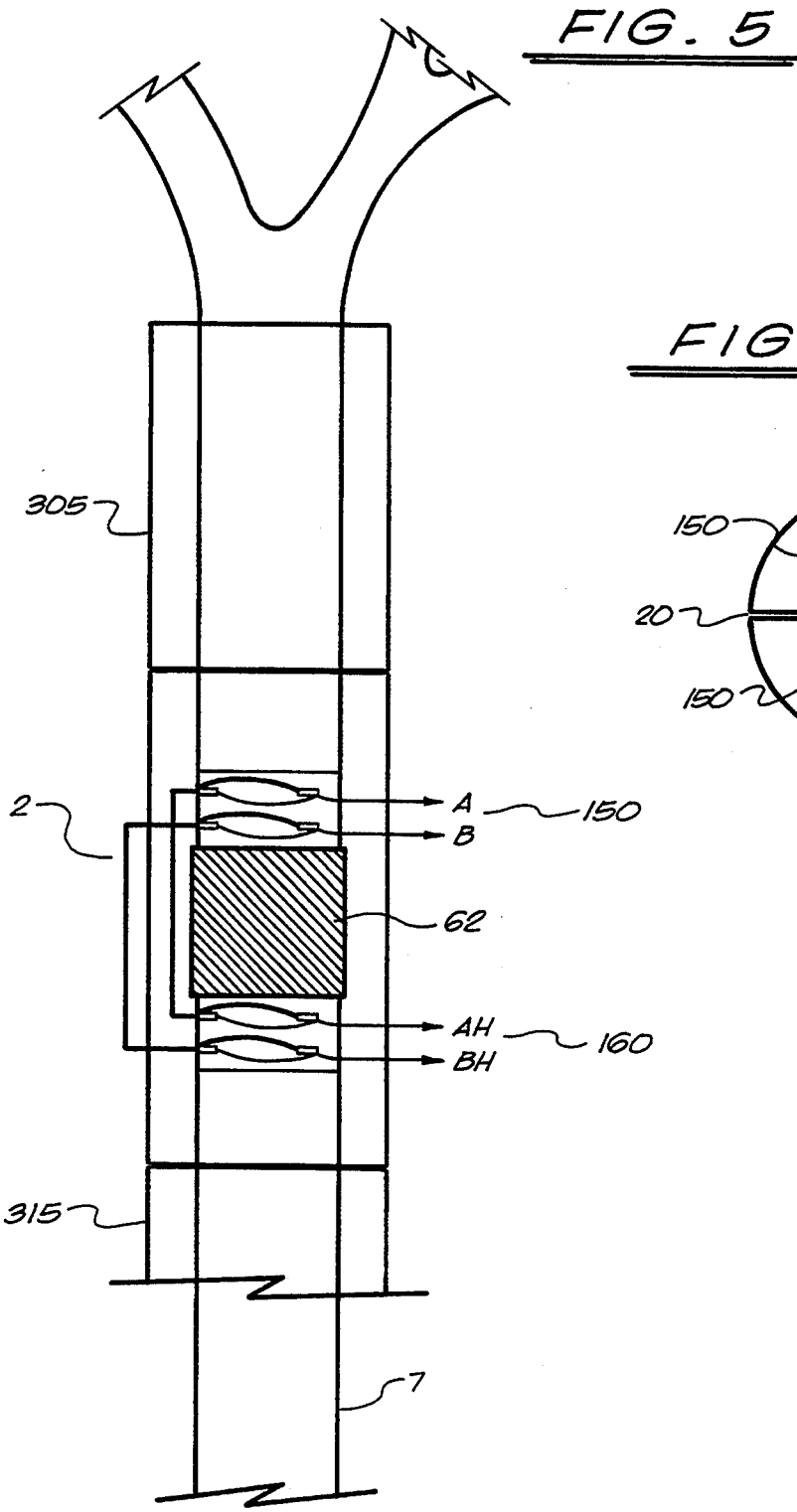
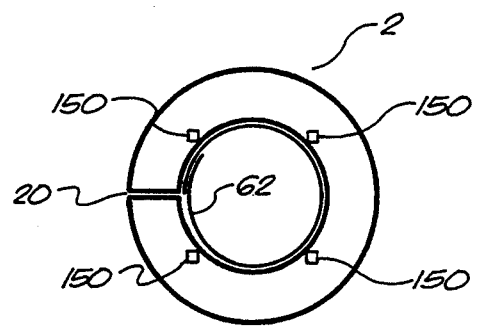
FIG. 5
FIG. 6

APPARATUS FOR MEASURING SAP FLOW

RELATED APPLICATIONS

The application is a continuation-in-part of pending U.S. application Ser. No. 07/741,293 filed Aug. 6, 1991 now U.S. Pat. No. 5,269,183.

FIELD OF THE INVENTION

The present invention relates to an apparatus for measuring the flow of sap in plants and the like, and more particularly relates to an apparatus for directly measuring sap streams in herbaceous plants and trees without the necessity for empirical calibration or stem intrusion.

BACKGROUND OF THE INVENTION

Accurate measurement and analysis of transpiration in herbaceous plants and trees is inherent in the effective growth thereof particularly under adverse environmental conditions such as in the desert and in underdeveloped countries. Unfortunately, the amount of water that is used by individual plants, shrubs and trees growing in indigenous fields, orchards, forests, or even urban landscapes, is not well known or documented.

Sap flow has been studied for many years by injecting heat into the stem of plants and trees. For example, the heat pulse velocity approach for measuring sap flow, suggested by Huber in the early 1930's. Another approach, the heat balance method, was suggested in the 1940's by German researchers and first implemented in Japan in the 1980's. See T. Sakuratani papers, "A Heat Balance Method for Measuring Water Flux in the Stem of Intact Plants" which was published in 1981 in J. Agric. Meteor. (Japan), vol. 37, pp. 9–17, and "Improvements of the Probe for Measuring Water Flow Rate in Intact Plants with the Stem Heat Balance Method" which was published in 1984 in J. Agric. Meteor. (Japan), vol. 40, pp. 273–277.

More recently, Sakuratani, in the paper entitled "Measurement of the Sap Flow Rate in Stem of Rice Plant" which was published in 1990 in J. Agric. Meteor. (Japan), vol. 45, pp. 277–280, disclosed his attempts to measure sap flow rate using a device designed to provide improved sensitivity and adequate thermal equilibrium between the heated sap and the stem surface. While an improvement of the prior art, this device was not portable inasmuch as its components were assembled in situ onto a plant's stem. Since this gauge was constructed with a simple thermopile located on either side of the stem, which in conjunction with its thermocouples were apparently shielded from the environment only by being wrapped by a sheet of glass fiber, the sap flow rates determined failed to accurately indicate the actual sap flow. The Sakuratani devise was also unable to accommodate stem growth and diurnal shrinkage and swelling.

In U.S. Pat. No. 4,745,805, Granier teaches a process and device for the measurement of the flow of raw sap in the stem of a plant. More particularly, there is provided a process for measurement of changes in the flow of raw sap in the stem of a plant, which comprises steps for insertion of two temperature-monitoring probes, supply of an electric current of constant intensity to the heating probe, and recording of the temperature difference between the two probes. The two probes are placed in the same stem separated by a distance such that the heat released by the heating probe can not appreciably affect the non-heating probe. The non-heating probe is preferably placed perceptively on the same vertical line as the heating probe, but underneath it. The Granier device also comprises a heating circuit stabilized by the heating probe, a thermal couple measuring means (the hot and cold junctions which are placed respectively in the heating and non-heating probes), and means of recording the voltage at the terminals of the temperature-monitoring device. The heating probe comprises a rigid tubular core on to which is wound a heating wire, which is in turn surrounded by a heat distributing tube made of a high thermal conductivity material such as aluminum, with the winding of the wire and the distributing tube being of a length approximately equal to the thickness of the sap-wood into which the probe must be inserted, and the tubular core containing one of the supply wires of the winding.

U.S. Pat. Patent No. 4,555,940, issued to Renger, discloses a method and apparatus for measuring and monitoring liquid flow rates and volumes in medical devices that pump liquids carrying medication into a patient's blood stream, spinal fluids, brain lymph glands and other organisms in the human body. The Renger apparatus includes a pyroelectric member for detecting or measuring changes in temperature of the fluid flow path and of the fluid as it passes through the temperature-modified part thereof. It is an aspect of this invention that the pyroelectric detector may be joined to the outside of the fluid flow path without penetrating therein, and thereby not impeding fluid flow therethrough. Particularly effective for tubular flow paths having a diameter in the range of 0.1 millimeter to about 5 millimeters, this apparatus measures and monitors both continuous and intermittent pulse liquid flow. The apparatus can verify the performance of the flow paths in tubular devices, warn of impending or existing unwanted changes in the rate of volume of flow, serve as a feedback system for monitoring flow at a predetermined rate or volume, detect bubbles, or some combination of these purposes.

More particularly, the Renger apparatus includes means for detecting changes in temperature as a function of fluid flow rates and volumes through the temperature-modified portion of the fluid flow path. This includes pyroelectric detector means such as pyroelectrically-sensitive polyvinyliden fluoride film. Pyroelectrically-sensitive film of this kind can be wrapped around the fluid flow path. For this apparatus to function properly, the pyroelectric detector means must be in close proximity to the temperature-modifying means in order to detect temperature changes reliably as the fluid flows through the temperature-modified portion of the fluid flow path. Preferably, the pyroelectrically-sensitive detector is joined to, and wrapped around, the fluid flow path. The detector should preferably be disposed upstream of the temperature-modifying means. Where pyroelectrically-sensitive polyvinyliden fluoride film constitutes the pyroelectric means, the metal film electrode on the pyroelectric film itself can also serve as temperature-modifying means.

In alternative embodiments, this apparatus can either include temperature-modifying means adapted to deliver a fixed quantity of heat, to change the temperature of the fluid flow path by a fixed amount for a fixed period of time, or simply to stop when a fixed temperature change has been attained. The temperature of the fluid flow passage before temperature modification begins is considered to be the reference or zero point. The temperature of the fluid flow passage is then modified to a pre-determined level before flow begins, and the temperature change is detected relative to the zero point. After fluid flow takes place to the temperature-modified portion of the fluid passage, the resulting temperature is detected as it relates to the fluid flow.

The energy balance method for measuring sap flow, well known in the art as the "stem heat balance" method, enables an absolute measurement of sap flow rate to be ascertained in the stems of intact plants or the trunks of woody species. See papers by T. Sakuratari published in J. Agric. Met. (Japan), vol. 37, pp. 9–17 (1981) and by J. M. Baker and J. L. Nieber published in Agric. For Meterol, vol. 48, pp. 93–109 (1989). According to this method, a stem section is continuously heated and the components of the heat flow are accurately measured. As known to those skilled in the art, provided that steady state conditions are sustained, this method affords accurate measurement of sap flow rates and inherently requires no empirical calibration but only a zero set determination before dawn. In addition, the energy balance method provides a continuous record of the sap flow rate and its accumulation over time. While the efficacy of this method has been demonstrated under controlled conditions in a greenhouse and the like, its applicability to diverse environments has been limited by the difficulty associated with isolating the sap flow gauges from the adverse effects of water intrusion, radiation, noise, etc. Thus, the prior art suffers from the inability to routinely and economically apply this methodology for measuring sap flow in the field.

Thus, Kitano discloses in U.S. Pat. No. 4,817,427 a device for measuring water flow rate in a plant stem but failed to deliver the features and reliability required in the field. This device requires in situ assembly of its various components, which include three heaters and three controlled power regulators to monitor the generated signals. Clearly lacking is the ability to protect the electronic components from intrusion by radiation and water, and to protect wiring from abrasion and other damage. Furthermore, this device does not appear to contemplate its non-destructive removal to enable repeated application thereof in the field. Related technology is disclosed by J. M. Baker and C. H. M. Van Bavel in their paper entitled "Measurement of Mass Flow of Water in the Stem of Herbaceous Plants" which was published in Plant Cell and Environment, vol. 10, pp. 777–782 (1987) and by S. L. Steinberg, C. H. M. Van Bavel and M. J. McFarland in their papers entitled "A Gauge to Measure Mass Flow Rate of Sap in Stems and Trunks of Woody Plants" published in J. Am. Soc. Hort. Sci., vol. 114, pp. 466–472 (1989) and "Improved Sap Flow Gauge for Woody and Herbaceous Plants" published in Agron. J., vol. 82, pp. 851–854 (1990).

A device for measuring fluid flow known in the art was disclosed by Poppendiek et al. in U.S. Pat. No. 3,336,804. Intended for fluid flow determinations in conduits, the Poppendiek device applied to measuring sap flow would require that a plant stem be cut into pieces. It should be clear to those skilled in the art that it is particularly advantageous for a sap flow measuring device not to invade a plant's surface. Winkler, in U.S. Pat. No. 4,384,578, teaches another device for measuring fluid flow using differential temperatures. The Winkler device, however, does not appear to be applicable to measuring sap flow in plants and the like inasmuch as no adaptability is provided for accommodating irregularly shaped stems, bending, or growth changes. In addition, as a biomedical sensor, it attempts to ascertain relative instead of absolute fluid flow rate, regularly requiring calibration. There also appears to be no provision for measuring radial heat loss, only for measuring a constant temperature differential across a heater surrounding a tube. To accurately measure fluid flow particularly subject to a diversity of environmental conditions in the field, there must be control of and allowance for this and other sources of heat loss.

Another procedure and apparatus for measuring fluid flow rates in conduits is taught by Detectif in French Pat. No. 761,973. More particularly, Detectif teaches a device with an electrically insulated sleeve which is hingedly clamped onto the circumference of a conduit, thereby causing contact between a thermopile's thermo-junctions and the conduit. The electrical potential generated from the thermopile is functionally related to the fluid flow rate. This device appears to ignore the axial conductive flow rate of heat carried by the fluid and the conduit's walls. Indeed, it appears that for useful fluid flow rate measurements to be made with this device requires calibration.

The sap flow means and techniques heretofore known by those skilled in the art fail to accurately and reliably ascertain the sap flow in plant stems and the like. Lacking is a device with electronic components capable of generating signals prerequisite to accurately represent sap flow. Also lacking is a device which adequately protects such electronic components from environmental influences including radiation and water intrusion. Accordingly, these limitations and disadvantages of the prior art are overcome with the present invention, and improved means and techniques are provided which are especially useful for ascertaining sap flow in herbaceous plants and trees.

SUMMARY OF THE INVENTION

As will be described in detail, embodiments of the present invention comprises devices for measuring sap flow in the stems of herbaceous plants and trees using the heat balance method known in the art. A device constructed under the teachings of the present invention comprises a housing which is insulated and sealed from intrusion from radiation or water. In one embodiment, a flexible housing is affixed to a foam insulating collar. The electronics comprising the preferred embodiment of the present invention are affixed to a cork substrate which is embedded within this flexible housing. In another embodiment of the present invention, which is particularly suitable for measuring sap flow in small diameter stems, a rigid housing, configured like a clam-shell, This embodiment is also intended to be contained within the foam insulating collar but is not fixedly attached thereto; instead, the collar sealably circumscribes the clam-shell after the clam-shell has been properly situated around the stem region being measured. In this alternative embodiment, the substrate is preferably constructed from a composite of foam tape and rubber gasket material to provide a means for the electronics to conform to a diversity of stem cross-sections and irregularities.

Using the relationships taught by the heat balance methodology, as will be hereinafter described in detail, the present invention incorporates temperature-sensing electronics to measure milliwatt energy transferred from an internal heater strip affixed to the substrate to the ambient, to the stem region, and to measure heat flowing up the stem. In accordance with the present invention, the heat transfer related to sap flow in a stem region is determined from four signals. Two signals are provided by two pair of differential thermocouples. Each differential thermocouple pair provides a signal indicative of temperature gradient above and below the heater and also indicative of conducted stem heat transfer. A third signal is generated from a thermopile, indicative of radial heat flux corresponding to heat loss to the ambient. A fourth signal is indicative of the millivoltage delivered to the heater.

Thus, under the present invention, sap flow is directly determined from four signals obtained from a novel arrangement of temperature sensing means; empirical calibrations are unnecessary. A portable, easily removable and reusable device powered preferably by a 0.2 to 5.0 watt heater is abuttably affixed to the periphery of a stem or trunk. A plurality of temperature sensors are embedded in a weatherproof collar and shield assembly, thereby protecting the integrity of the internally-generated four signals from inaccuracies due to invasion by radiation and water. These signals are preferably automatically processed by a small battery-operated recorder which also periodically stores in its memory the sap flow rate and the accumulated total thereof. These sap flow rate records may be obtained periodically for further analysis.

It is accordingly an object of the present invention to provide a means and method for measuring the sap flow in the stems of herbaceous plants and trees without prerequisite empirical calibration.

It is also an object and advantage of the present invention to determine the sap flow of herbaceous plants and trees accurately and non-intrusively.

It is also an object and advantage of the present invention that the sap flow of herbaceous plants and trees may be accurately determined by a convenient portable device using only four datalogger channels.

It is still another object and advantage of the present invention that various embodiments thereof may be effectively and optimally cascaded in dataloggers and multiplexors because of its unique four-channel design.

It is also an object and advantage of the present invention that the sap flow of herbaceous plants and trees may be accurately determined by a removable and reusable device.

It is an object of the present invention to accurately measure the sap flow of herbaceous plants and trees by providing an apparatus configured with electronics which inherently maintain close contact with the surface of the stem and the like.

It is a further object of the present invention to accurately measure the sap flow of herbaceous plants and trees by providing an apparatus which readily conforms to irregularities in the surface of the stem and the like.

It is still another object of the present invention to provide a device for accurately measuring sap flow rates in small diameter plant stems.

It is yet another object of the present invention to provide a device for accurately measuring low sap flow rates in plant stems and the like.

It is also an object of the present invention to enable convenient and accurate analysis of plant physiology in the field using a portable, inexpensive device.

It is also an object of the present invention to enable prediction of water consumption requirements for crops based upon similar soil characteristics, topology and weather conditions.

It is also an object of the present invention to provide accurate sap flow information for the design of drip and sprinkler irrigation systems in arid lands.

It is also an object of the present invention to provide accurate sap flow information for ascertaining water demand for crops grown in arid land under a diversity of seasonal and weather-related variations using a device constructed with electronic components adequately sealed and insulated from radiation and water-intrusion.

It is also an object of the present invention to provide sap flow information related to water management, hydrology and water quality studies for stream bank vegetation, phreatophytes, and such range land invaders as mesquite and cedar trees.

It is also an object of the present invention to provide convenient and inexpensive means for assessing root damage, insect damage, and even the degree of competition with weeds and the like.

It is also an object of the present invention to provide an accurate means of assessing the effect of air or water pollutants upon photosynthesis and respiration.

It is also an object of the present invention to provide an inexpensive means to monitor treatments intended to defeat cell destruction caused by water or air pollution.

It is also an object of the present invention to ascertain plants' growth patterns, fertilizer efficiency and resistance to drought.

It is also an object and advantage of the present invention that these four datalogger channel devices for determining the sap flow of herbaceous plants and trees may be mass produced affording a combination of cost and performance heretofore unknown in the art.

These and other objects and features of the present invention will become apparent from the following detailed description, wherein reference is made to the figures in the accompanying drawings.

IN THE DRAWINGS

FIG. 5 is a simplified partial cut-away front view of an embodiment of the present invention circumscribing a plant stem, depicting the electrical components thereof.

FIG. 6 is a top plan view of the electrical components depicted in FIG. 5.

DETAILED DESCRIPTION

Figure 1:
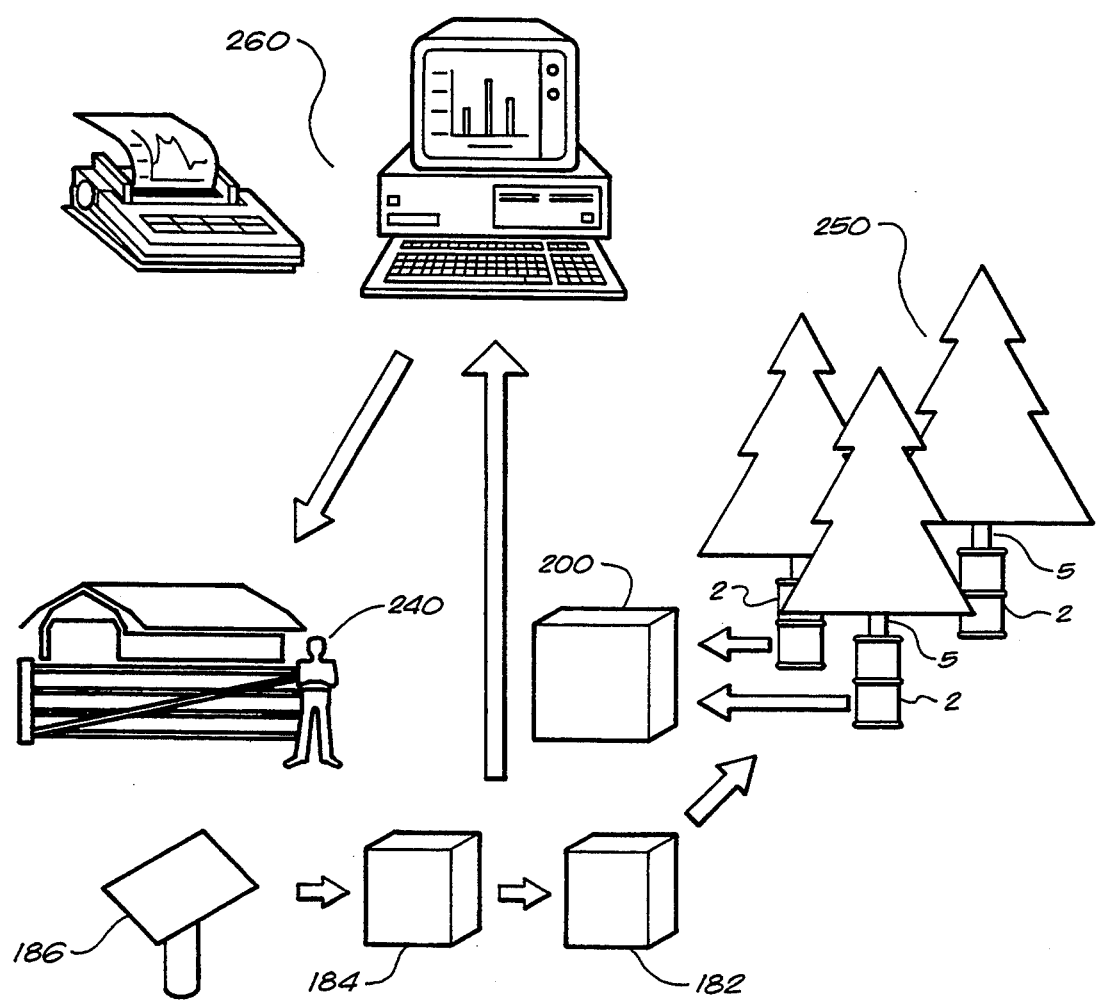
FIG. 1 depicts a system flow diagram depicting the operation of the present invention in the field.

Now referring to FIG. 1, there is shown a system flow diagram depicting the operation of the present invention in the field. Embodiments of the present invention, identified by the trademark "Dynagage" 2, are placed upon stems or trunks 5 in the field 250 and are powered either by d.c. power with a voltage regulator 182, a battery 184 and/or a solar panel 186. The temperature sensor signals are transmitted from gauges 2 to a suitable datalogger 200 and then analyzed via software using microprocessors 260 and the like. The results are then applied by workers in the field 240 for the benefit of crop growth and early warnings about such problems as root and insect damage and pollution.

According to stem heat balance method for measuring sap flow, a stem section is continuously heated and the components of the heat flow are accurately measured. In particular and referring to FIG. 10, the heat input $P_{in}$ is recorded as a radial conduction component $Q_r$, upward and downward axial or vertical conduction components $Q_u$ and $Q_d$, and vertical convective component $Q_f$. As will be described in detail, this convective transport rate is then converted to the sap mass flow rate based upon the corresponding rise in sap temperature.

Figure 4:
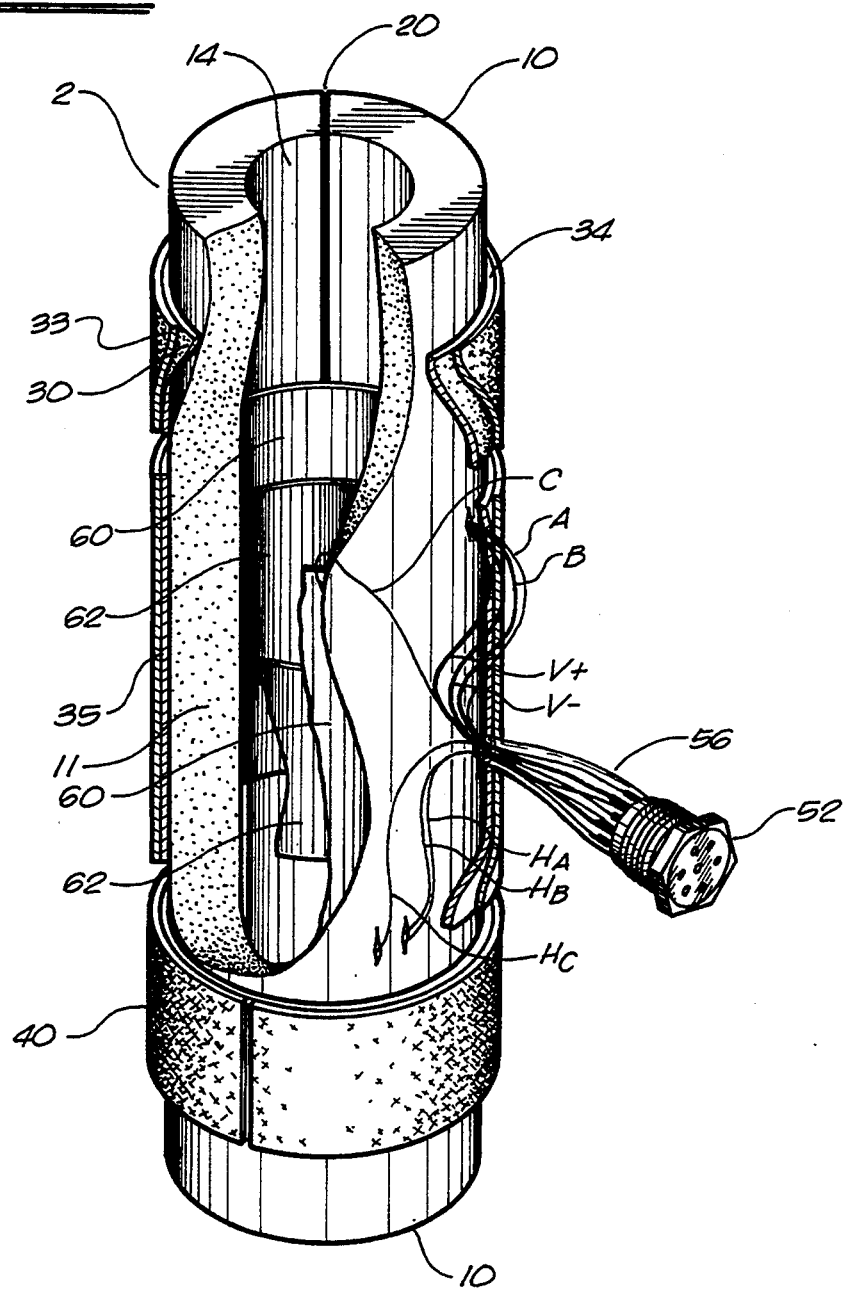
FIG. 4 is a frontal cut-away view of the embodiment depicted in FIGS. 2 and 3, showing the electronics assembly.

As is known by those skilled in the art, the energy balance method assumes that a steady state has been obtained and that constant energy is input from heater strip 62 within the body of gauge 2, depicted in FIG. 4. Accordingly, for the calculations to be properly applied, stem section 6 (FIG. 1) which engages gauge 2 must be insulated from environmental changes. Thus, it is advantageous for the gauge time constant to be within the range five minutes to one hour, depending upon the sap flow rate and the diameter of the stem.

Referring again to FIG. 10, the energy balance may be expressed as $$P_{in} = Q_r + Q_v + Q_f \qquad (1)$$

where the heater input, according to Ohm's Law, may be expressed in terms of its voltage and resistance $$P_{in} = V^2/R \qquad (2)$$

The axial or vertical conduction, $Q_v$, may be subdivided into an "upward" or $Q_u$ component and a "downward" or $Q_d$ component, which are expressed thusly by Fourier's Law:

$$Q_v = Q_u + Q_d \qquad (3)$$

$$Q_u = K_{st} A \, dT_u/dX \qquad (4)$$

$$Q_d = K_{st} A \, dT_d/dX \qquad (5)$$

where $K_{st}$ represents the stem thermal conductivity in Watts/meter-°K, A represents the stem cross-sectional area in square meters, dX represents the spacing between thermocouple junctions in meters, and dT/dX represents temperature gradient in either the upward or downward direction.

In accordance with the present invention, there are two differentially wired thermocouples, each measuring the rise in sap temperature. Still referring to FIG. 10, AH measures the temperature difference A-$H_a$ in millivolts. Similarly, Channel BH measures the temperature difference B-$H_b$ in millivolts. By subtracting those signals, the two components of axial heat conduction are isolated in terms of conveniently measurable quantities:

$$BH-AH=(B-H_b)-(A-H_a)=(B-A)+(H_a-H_b) \quad (6)$$

where B-A represents the upward axial conduction $Q_u$ and $H_a$-$H_b$ represents the downward axial conduction $Q_d$. Since the distance dX separating the upper thermocouple pair (A-B) and lower thermocouple pair ($H_b$-$H_a$) are constant and equal by design, equation (3) may be expressed:

$$Q_v = K_{st} A (BH-AH)/dX \quad (7)$$

and by converting millivolts into °C. using the factor 0.040 mV/°C., $Q_v$ is expressed as:

$$Q_v = K_{st} A (BH-AH)/dX*0.040. \quad (8)$$

In accordance with the preferred embodiment of the present invention, equation (8) has been implemented in a computer program which processes datalogger accumulated data to calculate the axial heat conduction in watts:

$$Q_v = \frac{K_{st} * A * (BH - AH)}{dX * .040 * 1 \times 10^4} \quad (9)$$

In equation (9), it should also be noted that the denominator thereof is practically entered as a single constant called the "temperature gradient conversion * area conversion." For example, the embodiment of the present invention identified as Dynamax SGA10 has a thermocouple gap of 0.004 meter and a corresponding constant of 1.60 in units of cm²-mV/m-°C.

As published by Sakuratani in J. Agric. Met. (Japan), vol. 37, pp. 9-17 (1981), and Baker and Van Bavel in Plant, Cell and Environment, vol. 10, pp. 777-782 (1987), the flow rate per unit of time, F, may be calculated from the following sap flow equation:

$$F = (P_{in}-Q_v-Q_r)/C_p*dT \quad (10)$$

The radial heat loss, $Q_r$, is calculated thus:

$$Q_r = K_{sh}*CH \quad (11)$$

where $K_{sh}$ represents the thermal conductance constant for a particular gauge installation as will be hereinafter described in detail; $C_p$ represents the specific heat of water in joules/gm-°C.; and dT represents the sap temperature increase. The temperature increase of the sap is measured in millivolts by averaging the AH and BH signals and then converting them to °C. by dividing the thermocouple temperature conversion constant, viz., $$dT = \frac{(AH - BH)/2}{.040} \quad (12)$$

It should be clear that the constant portion, corresponding to the "heat capacity/temperature conversion" constant, in the denominator of sap flow equation (10), is a combination of the hereinbefore explained temperature conversion and the heat capacity of water. To simplify the number of computation steps, it is advantageous for the datalogger computer program to combine these two constants thus:

$$4.186/0.40 = 104.65 \quad (13)$$

in units of joules/gms-millivolts.

Figure 9:
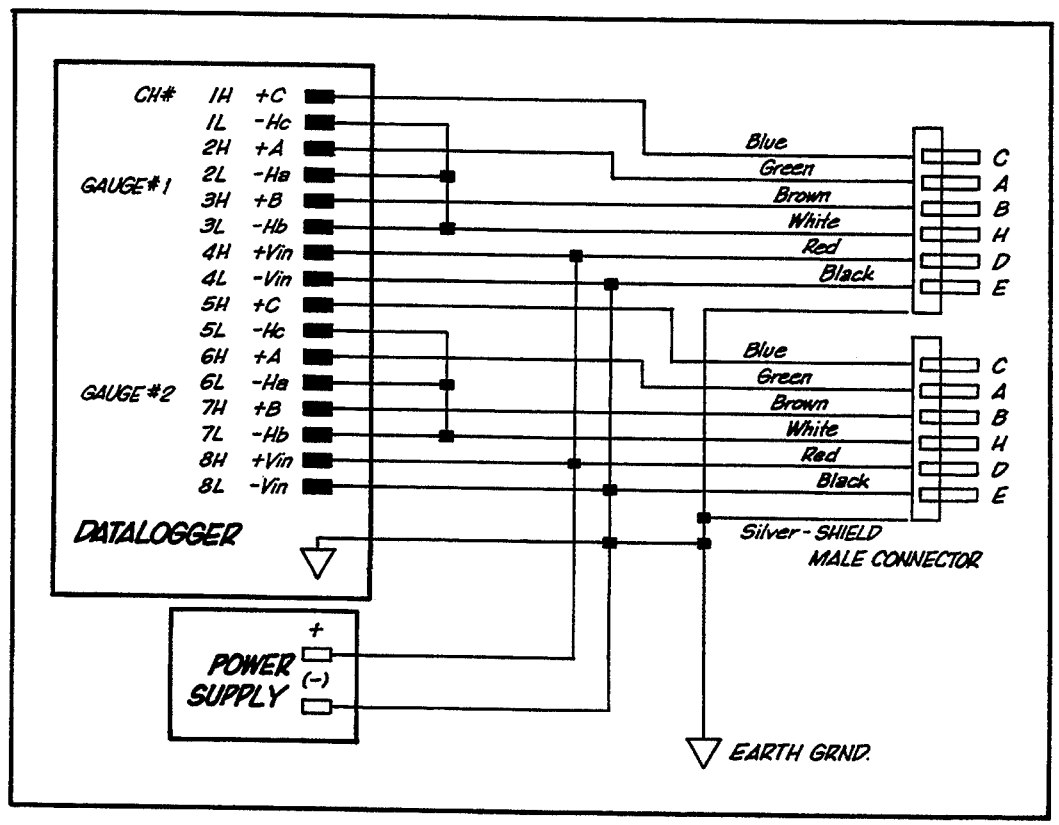
FIG. 9 depicts a schematic of typical wiring used for interconnecting two gauges embodying the present invention with a datalogger.
Figure 10:
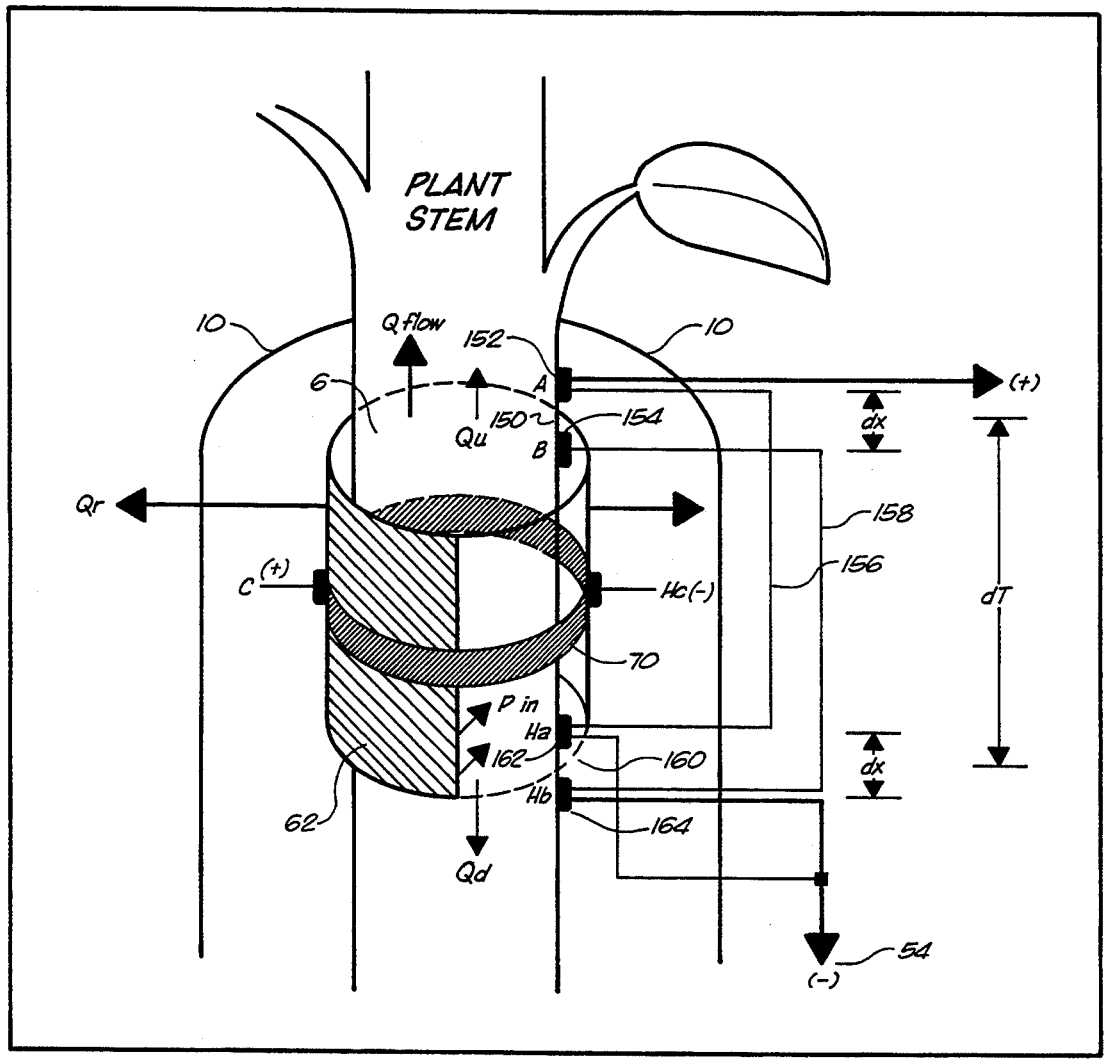
FIG. 10 depicts a schematic diagram depicting the components of heat transfer of a typical plant stem measured by the present invention.

The thermal conductance constant $K_{sh}$ for a stem with a fixed diameter may be related to the radial heat flux to the thermopile output CH thus:

$$Q_r = K_{sh} (E) = K_{sh} (CH) \quad (14)$$

since the signal E or CH input to the datalogger, as shown in FIG. 9, is directly proportional to the temperature difference between the inner and outer layers of the cork substrate. Signal CH is measured by the difference in voltage between C(+) and $H_c$(−), a reference as shown in FIG. 10. The basis for equation (14) which enables the estimation of Ksh is the thermodynamic relationship for the radial heat flux in a heated fluid contained in an insulated cylindrical section at a constant temperature:

$$Q_r = 2\pi K_{co} L (T_i-T_o)/\ln(r_i/r_o) \quad (15)$$

where $K_{co}$ represents the thermal conductivity of the cork substrate surrounding the heater, L represents the length of the cylindrical section, $r_i$ and $r_o$, represent the inner and outer radius of the cylindrical annulus, and $T_i$ and $T_o$ represent the corresponding inner and outer temperatures thereof. As will become apparent, the cork substrate typically embodies 8-12 thermopile junctions for enabling accurate measurement of the temperature both adjacent the heater ($T_i$) and the exterior of the insulating cork cylindrical annulus ($T_o$). This is shown schematically in FIG. 10, and in greater detail in FIGS. 18 and 19.

The sheath conductance is preferably calculated when a substantially "no flow" conditions exists. Thus, equation (1) is solved for $Q_f$=0, yielding $$P_{in} = Q_r + Q_v \quad (16)$$

and $$Q_r = K_{sh} (E) = P_{in}-Q_v \quad (17)$$

Accordingly, after computing $P_{in}$ and $Q_v$, as hereinbefore described, $K_{sh}$ is obtained thus:

$$K_{sh} = (P_{in}-Q_v)/E \quad (18)$$

As is known by those skilled in the art, apparent $K_{sh}$ is computed throughout the day and observed during installation on excised stems or under pre-dawn conditions, to obtain a minimum value. With respect to small diameter plants, a minimum $K_{sh}$ value may be assumed to occur simultaneously with a minimum flow rate, the zero set point. The minimum $K_{sh}$ occurs when CH is at its peak value, usually one to two hours before dawn. When the radial heat loss is at a maximum it is attributable to the convective heat flux being at a minimum. With respect to trees of typically large diameter, the $K_{sh}$ setting is more consistent when performed in an excised trunk or wooden post having the same diameter as the trunk.

By observing a plant's minimum apparent $K_{sh}$ value between midnight and an hour before sunrise, the constant $K_{sh}$ value to be entered as the zero set may be identified. Setting the zero in the case of small diameter plants should be performed on the plant whenever possible since it saves installation time and is also accurate.

As hereinbefore described, the sheath conductance is calculated when the plant establishes a non-flow condition. A value for $K_{sh}$ should preferably computed every sampling period and an average over 30 minute intervals. Apparent $K_{sh}$ calculations are of no use unless the sap flow is virtually zero. Thus, using equations (12) and (13), in which the radial heat flux, corresponding to the difference between the heat input and the axial heat conduction, measured in millivolts by the thermopile signal C-$H_c$; that is $K_{sh}$ ascertained by the equivalent relationship to that shown in equation (18) in which the thermopile signal is C-$H_c$ instead of E:

$$K_{sh} = (P_{in} - Q_v)/C\text{-}H_c \qquad (19)$$

Again, the minimum apparent $K_{sh}$ value is obtained at a minimum flow rate the zero set point. The minimum $K_{sh}$ will occur at the point when signal C-$H_c$ is near its peak value. It should be clear to those skilled in the art, when the radial loss is at a maximum it is because the convection heat flux is at its minimum or zero value. As is known in the prior art, each change of installation involving a change in stem diameter or major changes to the power input thereto causes a new $K_{sh}$ value to be manifest. Accordingly, after placing an embodiment of the present invention on a new plant, or after removing it for maintenance, the apparent $K_{sh}$ record should be reviewed for accuracy of the value thereof. See the publication by W. A. Dugas entitled "Comparative Measurement of Stem Flow and Transpiration in Cotton" published in J. Appl. Climatol (1990).

When sap flow is measured in a climate chamber, greenhouse, or inside a structure, as is known to those familiar with the art, the general recommendation for the zero set procedure is different. For example, on clear days shortwave radiation intercepted by leaves is the dominant factor causing transpiration. Typical solar radiation ranges from 500–1000 watts/$m^3$. In glass houses with clean and unobstructed ceilings, the radiation is typically cut by 10 to 15%. Another example, a plastic covered greenhouse is subjected to only 50% of the radiation level outside. In addition, while air movement is significantly lower inside than outside, the humidity experienced inside is significantly higher than outside. Thus, as a rule of thumb, transpiration is about 50% inside as opposed to outside. On the other hand, a heated greenhouse with augmented radiation from the heaters is an exception to this general rule.

In a growth chamber, the radiation is typically 150–250 watts/$m^2$. Air movement is minimal and thus transpiration is usually 20% of the same plant outside. When metal halide or sodium lamps are used, there is more energy available than with fluorescent lighting. Accordingly, to obtain 100 watts/$m^2$ with metal halide lamps, 400 watts of lamp/$m^2$ is installed no more than 0.5 meter above the plants.

Within in an office, home, or laboratory, the radiation levels are below 20 watts/$m^2$. In this case, stomata are only open occasionally or not at all. The water used from night to day will differ very little unless there is direct exposure thereof to sunlight. Inside the home or office, high carbon dioxide levels are generated by people breathing also reduces transpiration by partial stomatal closure. When people level and turn the lights off the transpiration does not significantly decrease because there is not much transmission anyway, and the humidity and temperature are normally unchanged.

Thus, it should be apparent that the usual outdoor methods for determination of $K_{sh}$ do not apply to indoor conditions. When the pre-dawn method is used outdoors, it is acceptable because the daytime flow rates are not very sensitive to the $K_{sh}$ settings. That is, the radial heat loss at that time becomes a small percentage of the total heat flux. If the plant is small, the high evening humidity, and negative vapor pressure gradients between the plant and the air cause only slight losses of water.

An alternative to this pre-dawn method is to enclose the entire plant and even the container, if possible, with a plastic bag. Essential to this method, however, is that the bag be air tight and remain in place during several hours of darkness until signals received from present invention indicate that stability has been achieved. Thus, the system comprised of the plant, the pot, the earth, and the present invention should arrive at thermal equilibrium. The assumption herein is that the humidity will rise to the highest possible level and that the plant is shielded from radiation and wind. Under these circumstances, $K_{sh}$ can be established with an accuracy in the range of 1–5% and the present invention will provide acceptable sap flow performance at the lower end of the flow range.

Another method is to use a section of excised stem or trunk of the same diameter as the plant or tree and to take zero flow ratings after equilibrium has been established as hereinbefore described. Results reported in the prior art indicate that similar results may be obtained from either of these alternative methods. See publication by S. L. Steinberg, C. H. M. van Bavel, and M. J. McFarland, published in J. M. Soc. Hort. Sci. vol. 114, pp. 466–472. As discussed therein, the sensitivity of the present invention to settings depends upon flow rates; it has been shown that a 10–20% variation in $K_{sh}$ causes only 4–9% variation in sap mass flow rate.

Figure 2:
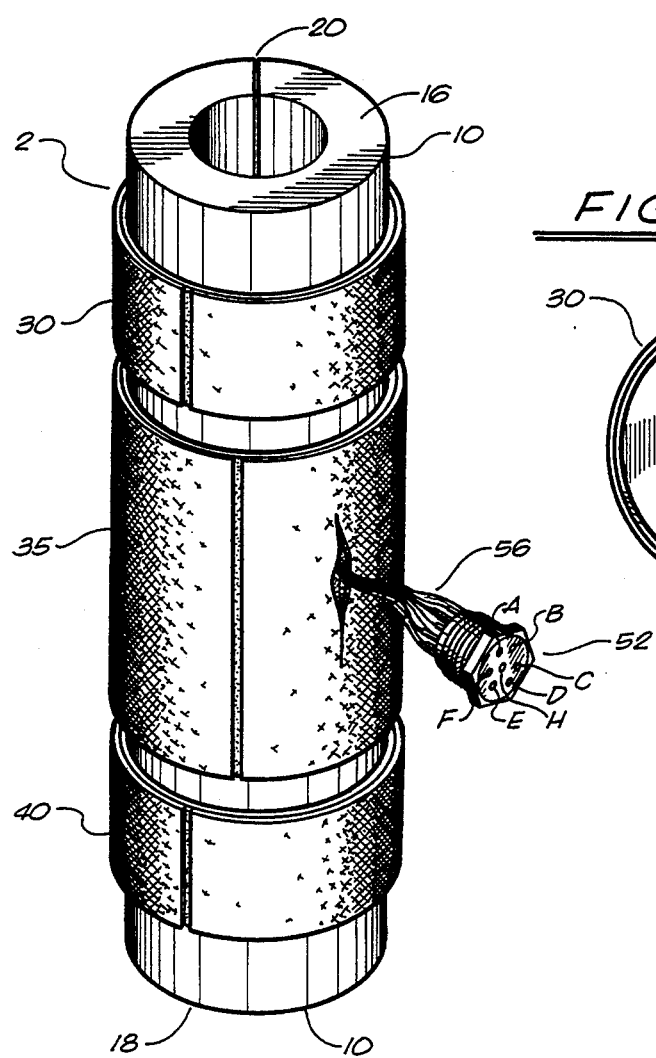
FIG. 2 is a frontal perspective view depicting a gauge embodying the present invention.
Figure 3:
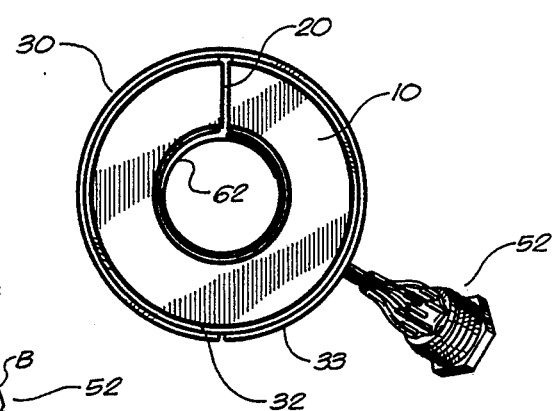
FIG. 3 is a top plan view of the embodiment depicted in FIG. 2.

Now referring to FIG. 2, there is depicted a frontal perspective view of sap flow measuring apparatus 2 comprising preferably soft-cell foam housing 10 circumferentially enclosing and insulating electronics assembly 50 (shown in FIG. 3). Housing 10 is preferably constructed from "Insultube," manufactured by Halstead of North Carolina, because of its closed-cell insulation properties attributable to small-diameter holes therein. In addition, the edges of Insultube are easy to seal with a coating like Halstead's "67×944" synthetic resin. This white resin is hand-painted on every housing surface, with its plurality of pores being appropriately dabbed with a paint brush. It should be noted that spraying or dipping the housing to achieve such a coating is ineffective because of its paint globs and runs causing unevenness. In accordance with the present invention, it is preferable to apply this white sealant coat to Insultubes' native black insulating tubes to prevent breaking down due to ultraviolet radiation or penetration into the cells by water from rain or condensation within the gauge. Thus, by coating Insultube as herein described, the apparatus is rendered outdoor rated.

Still referring to FIG.2, coated Insultube housing 10 releasably envelopes stem region 6 by fastener assembly 30. More particularly, the cooperation between upper Velcro fastener 30, medial Velcro fastener 35, and lower Velcro fastener 40 secure edge 16 of housing 10 to edge 18 across gap 20 thereof. Plug 52 interconnects electronics assembly 50 with datalogger 300 (FIG. 9).

In accordance with the present invention, preferably four datalogger channels are used to monitor the signals representing the sap flow computations. The present invention includes a novel electronic sensing method with three output channels per sensing device. Referring now to FIG. 3, the apparatus depicted therein senses milliwatt power transfers from heater strip 62 to the ambient, stem region 6, and also the sap flow which carries a varying amount of heat. As will be described in detail, two pair of differential thermocouples 150 and 160 (see FIGS. 5 and 10) provide two signals indicating the temperature gradient above and below the heater and concurrently measure the conducted stem heat transfer. A third signal, from thermopile 70, measures radial heat flux corresponding to the heat lost to the ambient. A fourth signal monitors the voltage to heater 62 so that the energy input thereto is known with precision.

Figure 7:
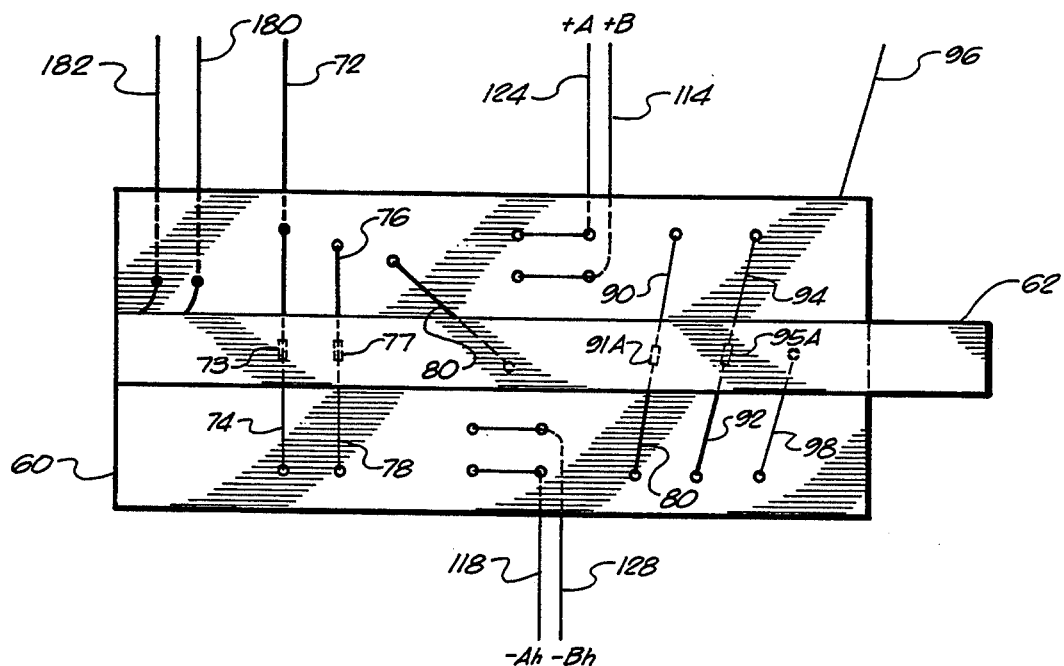
FIG. 7 is a front view of the electrical wiring embodying a thermopile in accordance with the present invention.

As shown in FIG. 4, an enlarged front view, of electronics assembly 50 depicted in FIG. 7, the electronics assembly comprises cork substrate 60 fixedly attached to internal wall 14 FIG. 4 of housing 10 and, in turn, pyroelectrically sensitive film 62, functioning as a milliwatt heater, disposed longitudinally of and fixedly attached to cork substrate 60. This pyroelectrically sensitive film 62, manufactured by Heater Designs of Cerritos, Calif., is comprised of Kapton and etched Iconel within a laminated flexible Mylar assembly and is attached to interior wall of housing 10 with E-6000 styrene-based clear, industrial grade adhesive manufactured by Eclectic Products, Inc. Like silicone adhesive, which is commonly used by those skilled in the art, E-6000 adhesive is flexible, paintable and durable. But unlike silicone adhesive, E-6000 provides satisfactory adhesion to Kapton or Mylar, and also provides sufficient strength for the bonding required in a gauge constructed in accordance with the teachings of the present invention. It should also be noted that cyano-acrylate ester adhesives like "super glue" are unsuitable for this application because they permit insufficient flexibility and are incompatible with porous materials.

Figure 8:
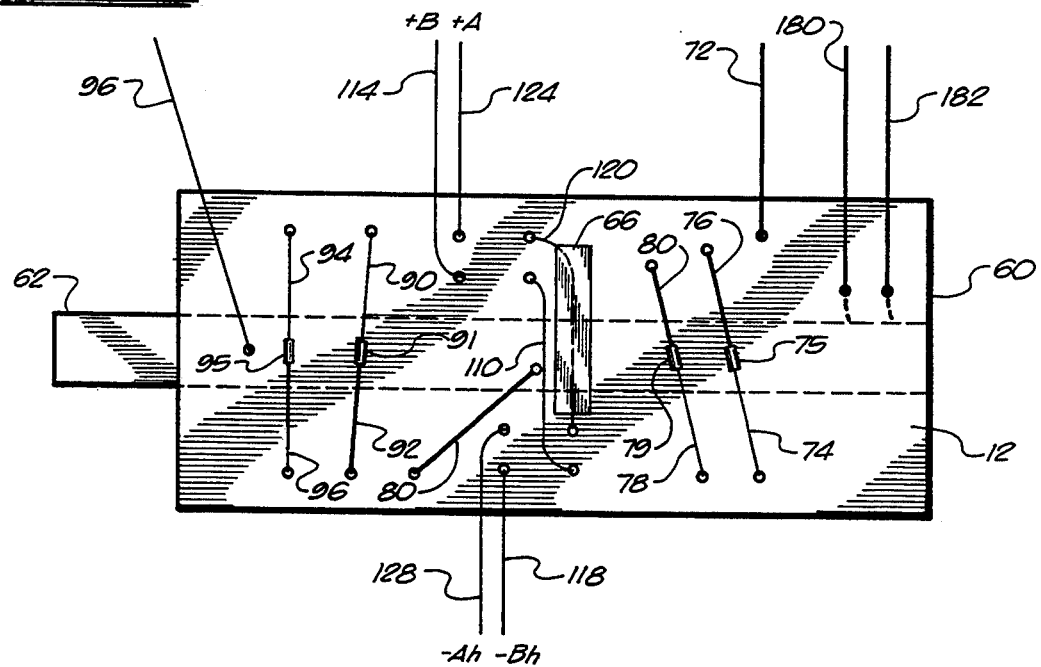
FIG. 8 is a rear view of the embodiment depicted in FIG. 7.

Cork substrate 60 comprises thermopile 70 which circumscribes heater 62. As depicted in FIGS. 7 and 8, thermopile 70 consists of a series of copper-constantan thermocouples connected in series. As is well known in the art, such a combination of copper and the alloy constantan provide a thermocouple with a high sensitivity above room temperature and maintain adequate sensitivity to temperatures as low as $-250°$ C. On such constantan product is manufactured by Omega Engineering, Inc. of Stanford, Conn. and identified as "Constantan." Specifically referring to FIGS. 7 and 8 depicting front and rear views of thermopile 70, there is shown series of thermocouples consisting of copper wire segment 72 connected to constantan wire segment 74 at junction 73, constantan wire segment 74 connected to copper wire segment 76 at junction 75, copper wire segment 76 connected to constantan wire segment 78 at junction 77, constantan wire segment 78 connected to copper wire segment 80 at junction 79, copper wire segment 80 connected to constantan wire segment 90 at junction 91A, constantan wire segment 90 connected to copper wire segment 92 at junction 91, copper wire segment 92 connected to constantan wire segment 94 at junction 95A, constantan wire segment 94 connected to copper wire segment 96 at junction 95, and copper wire segment 96 connected to connector wire. Each of these junctions are seen to be alternately adjacent heater 62 and exterior surface 12 of cork substrate annulus 60. Cables 180 and 182 are connected to the positive terminal of power supply 184; cable 98 is connected to the negative terminal thereof. Kapton tape 66 insulates copper wire segments 110 and 120 from each other.

Power supply 184 may be a 12 volt marine battery that is regulated to the appropriate gauge power setting, as will be hereinafter described. A DC-to-DC voltage regulator, e.g., Dynamax models AVR-3 or AVR-6 (182), may be used to adjust the power to the initial settings for stem-gauge embodiments of the present invention, viz., 3–5 volts, or for trunk-gauge embodiments, viz., 5–9.5 volts. Of course, if AC power is available, a line-operated adjustable DC supply may be used, provided that such power is steady and is substantially free from large daily fluctuations. For example, Dynamax power supply model DPV120 has a current rating of 3 amps with load regulation less than 0.1 volt from zero to full load and concomitant line regulation of 0.1 volt from 105–135 VAC. With a ripple of less than 0.005 volts rms, the DPV120 also has a current protection setting and affords protection if shorts occur.

As should be apparent to those skilled in the art, the power supply for field applications of the present invention where there is no line power available may be accomplished by periodically manually recharging batteries or automatically recharging them using solar power. In the latter recharging method, the solar panel must be sufficiently sized to have the capacity to replace the number of amp-hours consumed by an apparatus constructed in accordance with the teachings of the present invention and recording equipment, allowing for a worst-case on-site sunlight scenario. For example, using model MSX53R manufactured by Solarex, which has the capacity to output 3 amps of current at peak output, in a climate like South Texas affording 5 solar hours during winter, there would be available an equivalent of 15 amp-hours in the worst case. Thus, for 24-hour operation, the maximum continuous drain is 15/24 or 0.625 amps at 12 volts.

Now referring to FIGS. 2 and 9, there may readily be seen the communication of the four signals generated during the operation of a gauge with datalogger 200 through plug 52, in accordance with the present invention. In particular, the electrical connections depicted in FIG. 9 as C, A, B, H, D, and E correspond to the likewise identified connections on plug 52 depicted in FIG. 2. Color-coded wires 56 in FIG. 2 are particularly identified in the schematic depicted in FIG. 9.

Relating FIGS. 9 and 10, there is seen signal CH measuring the temperature differential across gauge 2 from the interior of thermopile junctions shown as $C(+)$ to the exterior thereof at $H_c(-)$. Signal DE measures the voltage input to heater 62. Signal AH is responsive to the temperature differential measured across constantan wire 156 between thermocouple 152 disposed above heater 62 and thermocouple 162 disposed therebelow. As clearly shown in FIG. 10, this first of two temperature differentials corresponds to thermocouple signal A-Ha. Similarly, signal BH is responsive to the temperature differential measured across constantan wire 158 between thermocouple 154 disposed above heater 62 and thermocouple 164 disposed therebelow. As clearly shown in FIG. 10, this second of two temperature differentials corresponds to thermocouple signal B-Hb.

Without deviating from the concept of the present invention, as shown in FIGS. 5 and 6, alternative embodiments thereof may be constructed with different number of temperature sensors on its circumference and with different number of thermopile junctions circumscribing the heater. As should be apparent to those skilled in the art, embodiments of the present invention intended for application to tree trunks require more power to generate the representative signals, than embodiments intended for application to plant stems and the like. More particularly, the combination of gauge 2 with sealing collars 305 and 315 abutting above and below, respectively, are shown disposed annularly of tree trunk 7. The embodiment shown has eight pair of thermocouples for sensing the temperature differential across heater 62.

It is a feature of the present invention that signals emanating therefrom are typically in the range $-100$ $\mu V$ to $+100$ $\mu V$, corresponding to small temperature differences on the order of $-2.5°$ C. to $+2.5°$ C. Accordingly, in accordance with the preferred embodiment of the present invention, datalogger 200 should preferably have a resolution of 1 $\mu V$ and differential input measurement capability, i.e., low noise characteristics. For example, dataloggers manufactured by Campbell Scientific Inc., identified as 21X and CR7, may be used, and are supported by software.

As should be apparent to those skilled in the art, prerequisite to acquiring accurate sap flow measurements is the alleviation of sources of thermal noise. Excess bark should be removed and the stem cleaned; dirt and dead bark impede the proper sensing of temperature. Small amounts of insulating silicone compound should be applied to the stem to remove air pockets, thereby improving heat transfer to thereto. It is also preferable to securely install the heater using approved silicone electrical insulating compound.

Once the instant apparatus is secured to the properly prepared stem region, weatherproofed foam collars and an aluminized shield should preferably be attached. The shield should preferably be constructed from a composite sheet with aluminum contained on the exterior and polyvinyl chloride contained on the interior thereof. Moisture and mating points should be sealed using silicone compound adjacent the collars. In addition, layers of aluminum foil may be wrapped around exposed trunks and stems especially from gauge to ground level. It is also advantageous to mount gauge temperature sensors away from scars, petiole nodes, and graft marks, to assure sufficient contact between the sensors and the trunk or stem surface. Thus, the exclusion of external heat sources particularly emanating from the sun, and large temperature gradients originating at the base of a plant, will tend to eliminate or at least minimize thermal noise.

Figure 15:
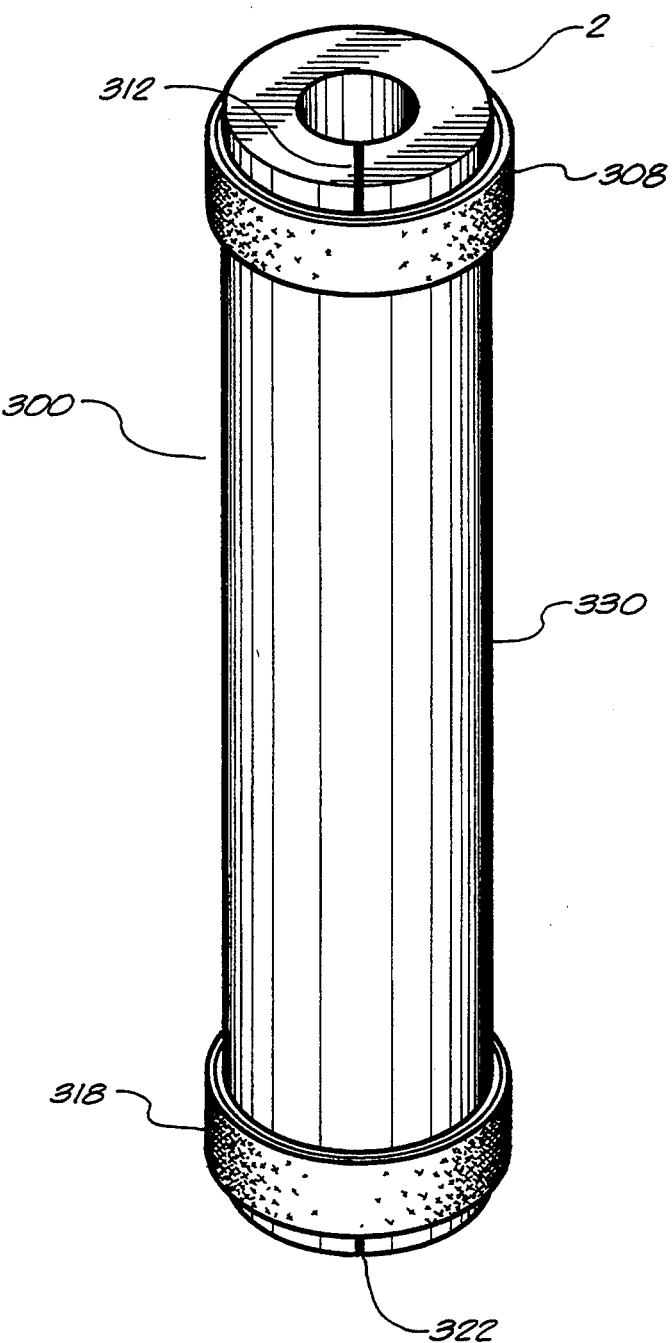
FIG. 15 is a frontal perspective view depicting a weather shield assembly embodying the present invention.
Figure 16:
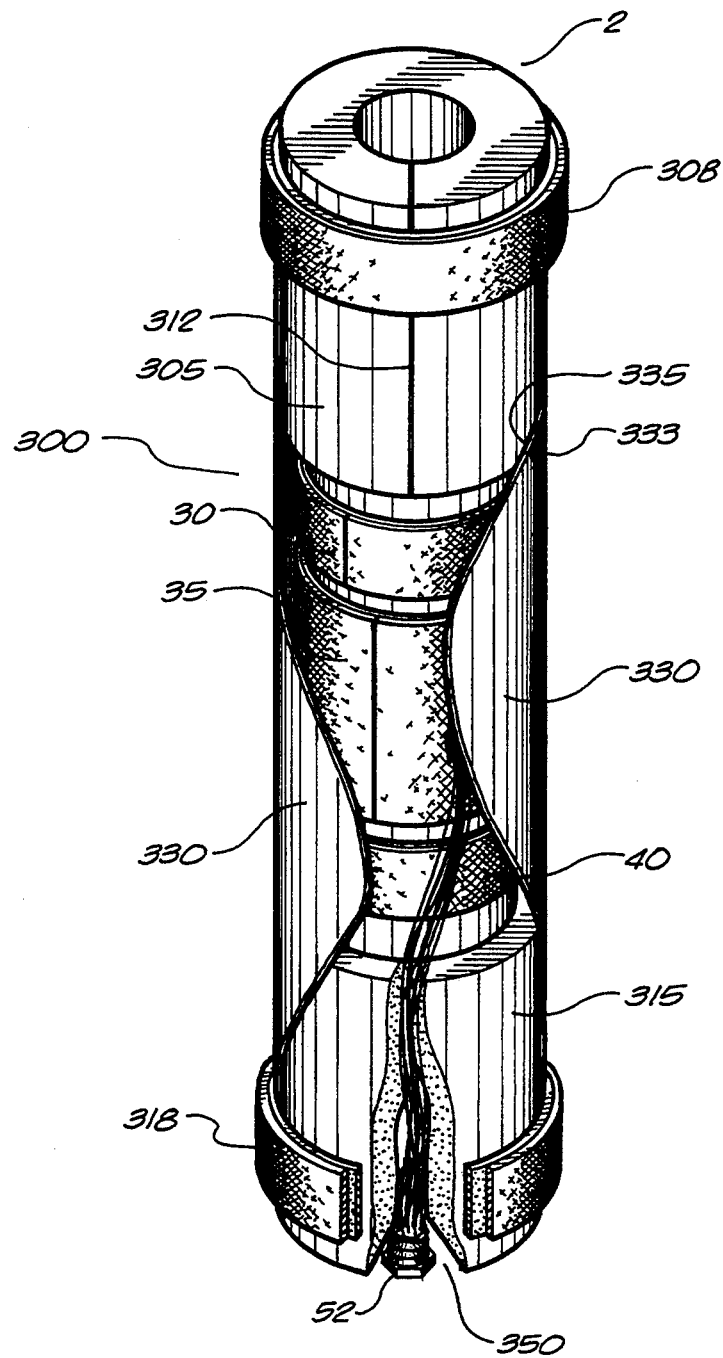
FIG. 16 is a cut-away view in partial cross-section of the weather shield assembly depicted in FIG. 15.

In accordance with the present invention, a preferred apparatus is provided which affords insulation and protection from adverse conditions under diverse environments. Referring to FIGS. 15 and 16, there is depicted a unique weather and environment protective assembly 300 for maintaining steady state conditions during the operation of sap flow gauges embodying the present invention. In particular, there is shown upper collar member 305, lower collar member 315 and medial shield member 330, cooperating to insulate gauge 2 from environmental conditions. Collar members 305 and 315 are releasably and sealably secured to gauge 2 by Velcro straps 308 and 318, respectively.

Collar members 305 and 315 are preferably constructed from Insultube coated with 67×944 resin for the reasons hereinbefore described in detail. Shield member 330 is preferably comprised of an aluminum—polyvinyl chloride composite sheet, e.g., Vinalum manufactured by Proto Corp. of Florida, for protection from longwave radiation and other environmental nuisances. Shield member 330 is configured to be abuttably and sealably received by the bottom edge of upper collar member 305 and the top edge of bottom collar member 315.

Now specifically referring to FIG. 16, there is seen a cut-away view of gauge 2 protected by weather shield assembly 300. Upper collar member 305 is configured to be abuttably received by the top edge of upper Velcro fastener 30 and to be in a sealable relationship therewith. Similarly, lower collar member 315 is configured to be abuttably received by the top edge of bottom Velcro fastener 40 and to be in a sealable relationship therewith. Longitudinal channel 350 is contained in collar member 315 for sealably receiving plug 52 for communication with datalogger 200.

One underlying assumption of the gauge physics is that operation occurs in steady state conditions. Any event which causes a deviation from this state may induce anomalous readings until steady state conditions are reestablished. There are situations where the gauge measures a change from the initial conditions of zero-flow to a high flow rate during the first hour of sunlight. A rapid warming of the stem or trunk occurs simultaneously, and either of these conditions can cause readings to fluctuate with over-estimates or negative flow. Another example of aberrance to the steady state is a sun angle perpendicular to the trunk of a tree just before sunset. The incident should be coming from the heater. These problems which vary by the species and the local environment, as well as may other potential difficulties, can be reduced or eliminated when one is knowledgeable about the normal heat fluxes and temperatures required for operation.

Figure 11:
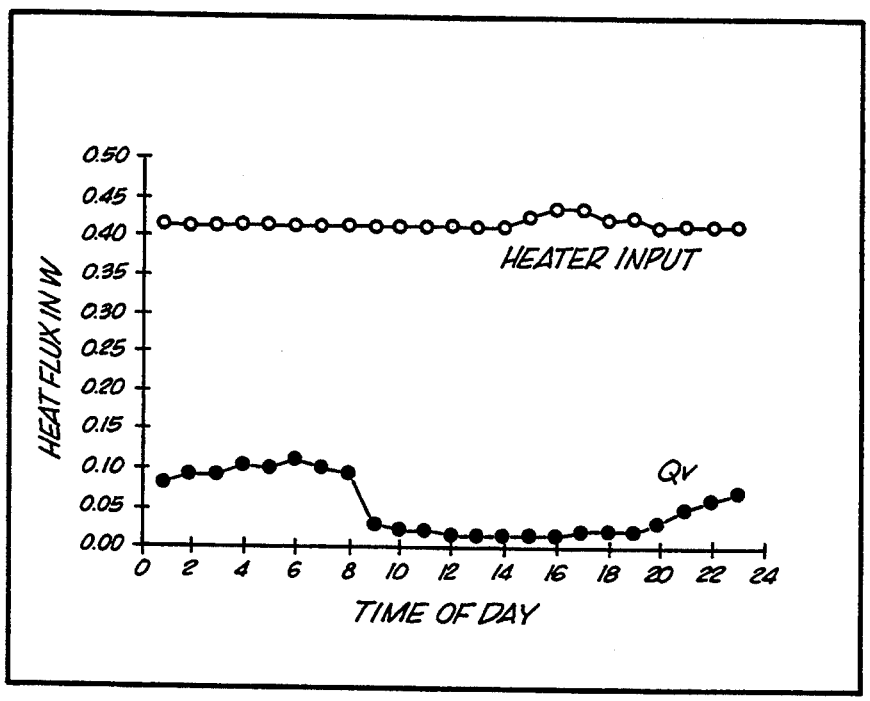
FIG. 11 depicts a plot of vertical heat flux vs. time of day in a tree trunk.

FIG. 11 shows the operation of an embodiment of the present invention on a 35 mm diameter bald cypress, Taxodium Distichum. As shown in FIG. 11, the vertical conductive heat flux varies from 25% of the total input power (0.4 W) in the dark hours to a very slow (2.5%) percentage during the day.

Figure 12:
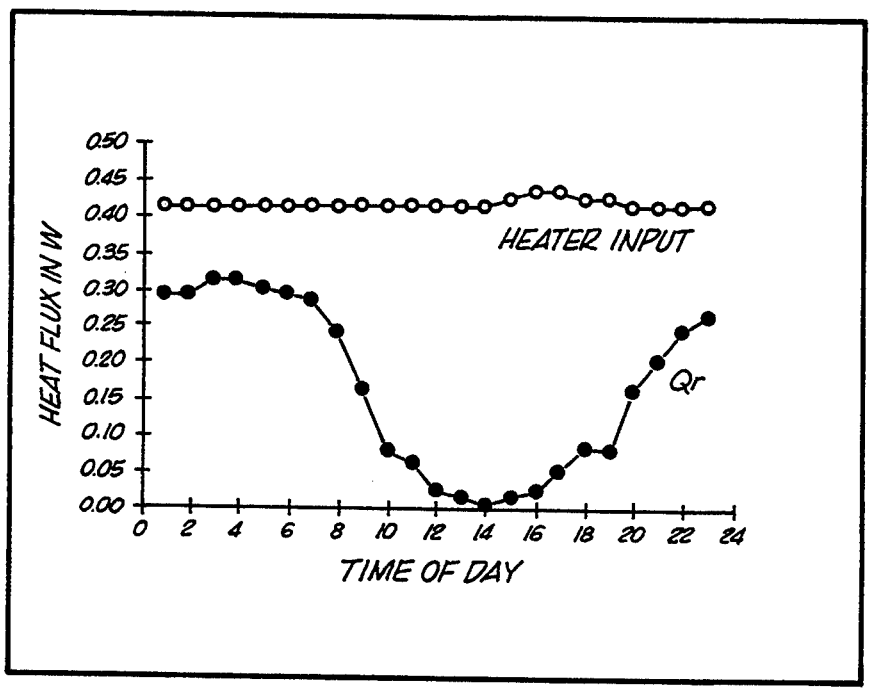
FIG. 12 depicts a plot of radial heat flux vs. time of day in a tree trunk.

FIG. 12 shows the radial heat flux, Qr, as a function of time. Note that the peak in radial flux occurred from 3:00 to 4:00 a.m. At that time the apparent Ksh value was confirmed to be its correct value. Shortly, after sunrise, the radial flux begins to drop, and finally at 14:00 hours, the radial flux approached zero. Then Qr begins to rise as the sap flow decreases during the late afternoon and evening.

Figure 13:
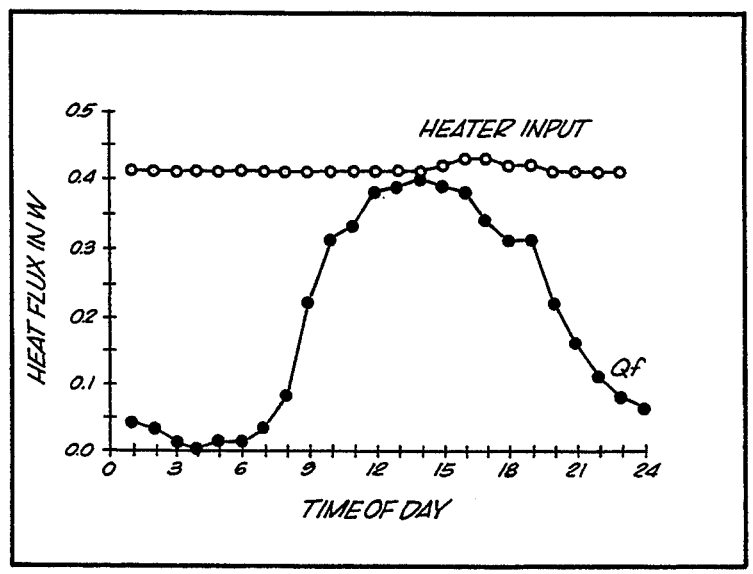
FIG. 13 depicts a plot of convective heat flux vs. time of day in a tree trunk.

After performing the energy balance computations, the resulting convective heat flux, Qf, is charted in FIG. 13. This chart shows the net power absorbed by the sap flow. Observe that in the hottest part of the day, nearly all of the heat supplied to the trunk is carried by the sap.

In some cases, radial flux during the day may become negative, indicating that more power is being added to the system by the ambient since the sap temperature may be below the surrounding air and gauge temperature even after heating by the gauge. These conditions are not necessarily a cause for concern, and it has been shown that this causes no degradation on overall gauge performance.

Figure 14:
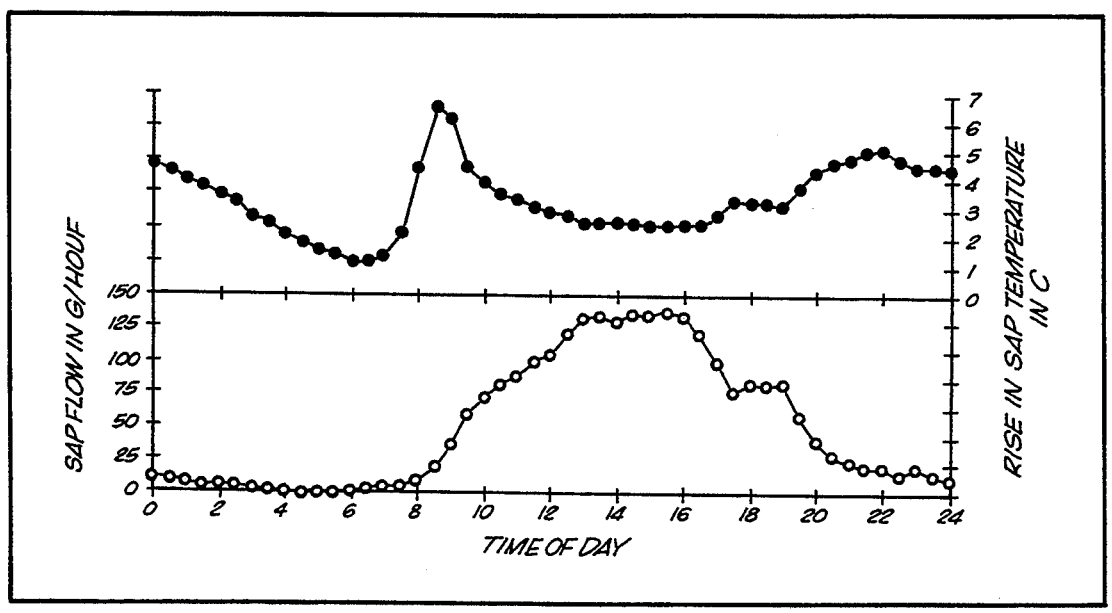
FIG. 14 depicts a composite plot of rise in sap temperature and sap flow vs. time of day in a tree trunk.

The diurnal cycle of the sap temperature increase and the resulting mass flow are charted in FIG. 14 as a function of time. The sap temperature increase, dT, reaches its peak just after sunrise and is the result of the non-flowing sap which was heated overnight moving up the trunk. This causes a temperature about 2.5 C. higher than the dT found at the same level of sap movement during the evening at 20:00 to 22:00 hrs.

As the day progresses, the dT decreases due to the faster movement of water. When a chart is crated to show the relationship of sap temperature rise versus the flow rate, the relationship becomes very clear. FIG. 15 is very useful as a tool for understanding the dT cycle, and is important in the explanation of signal analysis contained in the following section.

Several observations are made concerning the sap temperature increase. First, the temperature from zero to 10 g/hr flow has significant 4 C. change. Also note that dT never went to zero, as one might expect if the flow if sap stopped for more than an hour or so. The conclusion is that sap flow never stops completely. In so far as the magnitude of flow compared to the daily total is very insignificant, there is no great need to adjust Ksh for the user interested in daily water consumption. Another observation is that the temperature increase of almost 7 C. from 08:00 to 09:00 indirectly shows how hot the epidermis is becoming. In general, a temperature increase of 8 C. is considered dangerous to plant tissue. The customer must qualify this parameter on is own, because of the wide variations in the physiology of species. A further observation is that the dT during the highest flow periods of the day was never less than about 2.5 C., a signal easily measured and two orders of magnitude above the normal noise margins and resolution found in Dynamax dataloggers. In conclusion, it is prudent to reduce the power in the cause of the bald cypress in a natural setting, because there is more than enough signal strength available to measure the sap flow rate which would be considered low flow in comparison to other species in hot and dry climates.

Figure 17:
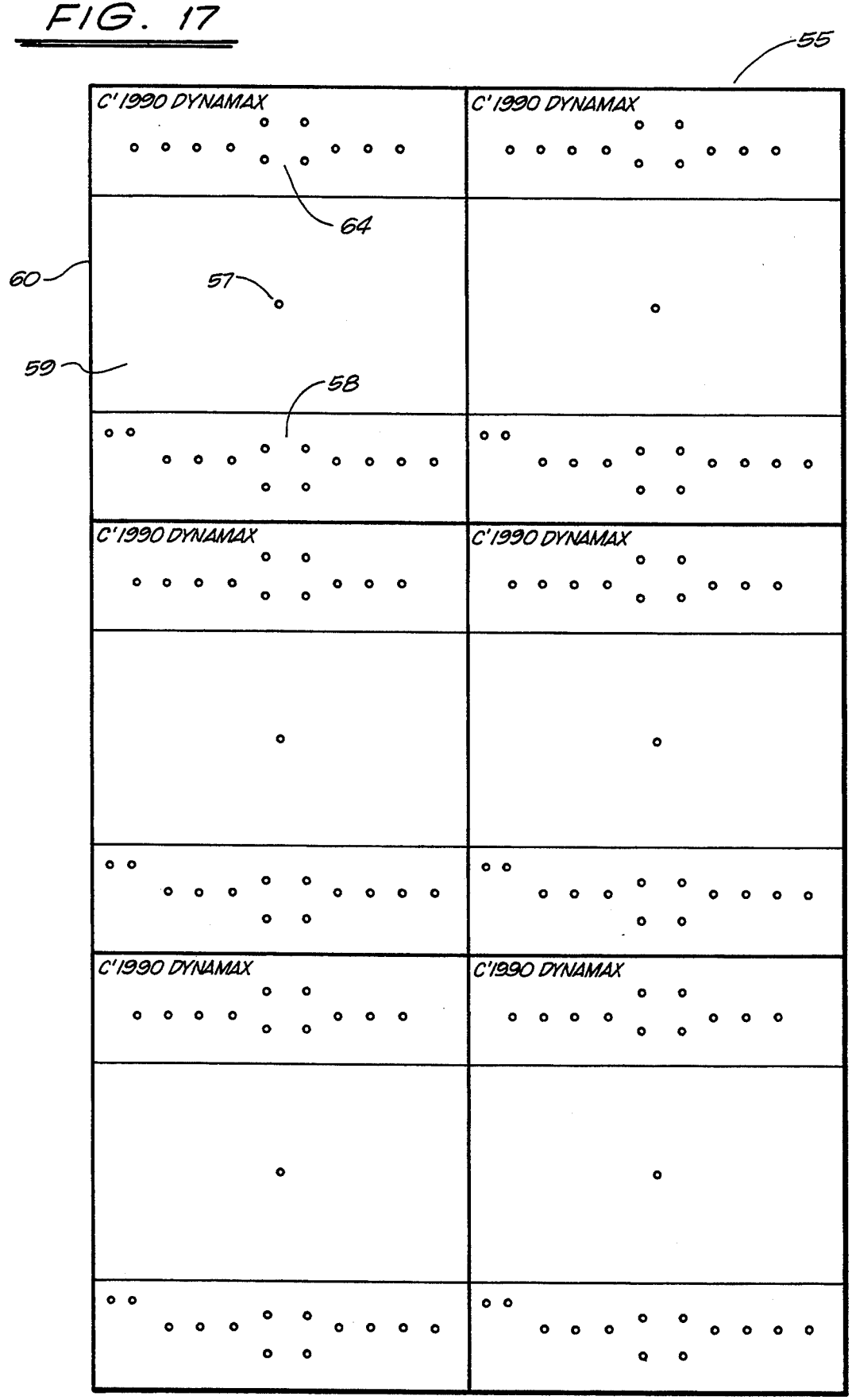
FIG. 17 depicts a cork substrate configured in accordance with the present invention.

It is within the teachings of the present invention to provide a method for the production of improved sap flow gauges which are not only inexpensive, but also reliable. The first step consists of printing a repeated pattern on a preferably neoprene-impregnated cork substrate, substantially 1/16" thick, preferably using a silk screen process. Each pattern for a specific size gauge is contained on a separate sheet, thereby eliminating having to hand-draw each pattern or to individually place and measure each position of thermocouple junction. Pattern 60 for the preferred embodiment is shown in FIG. 17. As clearly depicted therein, cork sheet 55 comprises six repetitions of pattern 60. In particular, pattern 60 consists of heater hole 57 located within shaded area 59 for receiving heater 62, upper plurality of holes 64 and corresponding lower plurality of holes 58. This printed pattern is then allowed to dry as in conventional in the art.

Next, plurality of wiring holes are drilled into the cork using a prepared numerical controlled drill pattern. Each hole is drilled to the size of a thermocouple junction, preferably 1 mm wide.

The next step is to cut dowel stock of appropriate diameter into proper size and to finish the ends thereof. For convenience and illustrative purposes, production of the Dynamax 25 mm gauge identified as SGB25 will be described. 1⅛" wooden dowels are cut to 270 mm length and the ends thereof sanded. In accordance with the present invention, each gauge is manufactured on the dowel to conform to the shape of the round stem. The dowel is shipped with the completed gauge to maintain the preferable cylindrical cross section thereof.

Next, Insultube, as hereinbefore described, is configured by cutting into 1⅛ ID×½" wall lengthwise (6 ft sections all at once) into the wall with a circular saw to make opening 20 of housing 10 (FIG. 2) to receive gauge electronics assembly 50. Insultube is also cut into 110 mm lengths with a sharp blade and miter guide or band saw to make each length with orthogonal edges 16 and 18 (FIG. 2).

The next step is to clean the talc used in the extruding process from the inside of the tube. The weather coating will not adhere if the tubing is dirty.

The cleaned Insultube is then painted on all surfaces thereof with two to three coats of white latex rubber weather proofing. As hereinbefore described, such coating reflects heat, sheds water, and provides a surface for adhesives to stick securely. Gauges and Insultube tubing are not outdoor-rated without the coating. The paint is then allowed to dry as is conventional in the art.

Next, Insultube is configured by cutting upper collar 305 and lower collar 315 for weather shield assembly 300 (FIG. 16). 1⅛" ID×¾" Insultube is preferably used and cut slit (312 and 322 in FIGS. 15 and 16) vertically to sealably receive housing 10 (FIG. 16), and then cut lengths 80 mm. The collars are then prepared in accordance with the hereinbefore described cleaning, painting, and drying steps.

The next step is to prepare Velcro straps. Cut two 2" wide white Velcro straps from roll. Hook straps are 7" long, and loop straps are 7½" long. Then, using E-6000 styrene based glue, as hereinbefore described, glue two loop straps to the middle of the gauge insulation collar (FIG. 16). Cut two more ¾" wide straps for the upper and lower weather shield collar, and glue the loop straps next to one end of the upper and lower collars.

Figure 19:
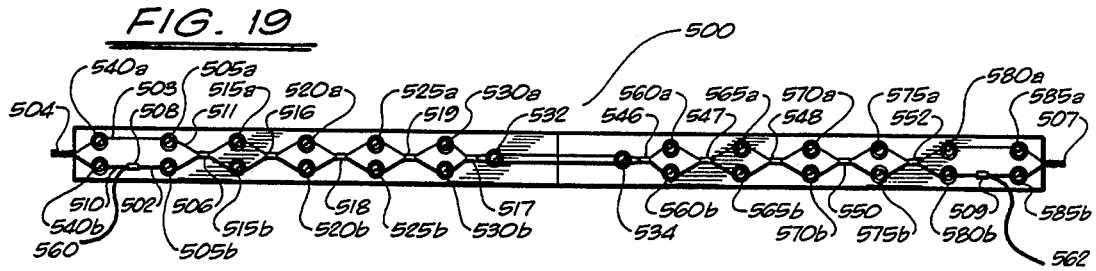
FIG. 19 is a top view depicting a thermopile wiring board for constructing constantan-copper wire in accordance with the present invention.
Figure 20:
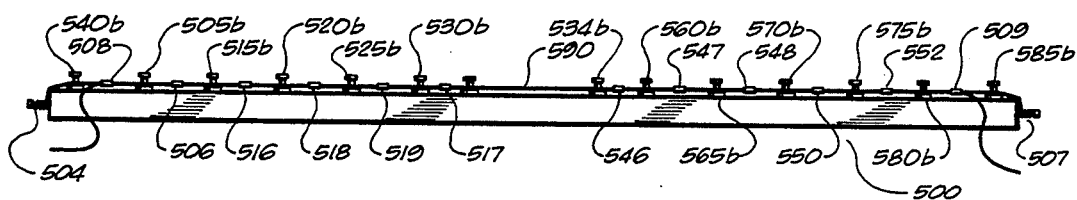
FIG. 20 is a front view of the wiring board depicted in FIG. 19.

In the next step and referring to FIGS. 19 and 20, composite wire for threading thermopile 70 is prepared using jig 500. In particular, bare 0.010 "copper wire 503 and bare 0.010" constantan wire 502 are used to create composite thermopile wire thread 550 shown in finished form in FIG. 20. One end of bare copper wire 503 and one end of constantan wire 502 are affixed to wire holder nail 504 and pull each across set of wire guide pegs 540a–b and around first set of wire guide pegs 505a–b. That is, copper wire 503 is pulled across guide peg 540a and around guide peg 505a. Similarly, constantan wire 502 is pulled across guide peg 540b and around guide peg 505b. A half twist is then made in each wire so that copper wire 503 and constantan wire 502 form junction 506, with both wires remaining on the same side of jig 500's longitudinal axis as when they started. Similarly, each wire is then pulled around the next set of wire guide pegs 515a–b, and given then a half twist to form junction 516. Similarly, junctions 518, 519 and 517 are formed by performing half-twists of copper wire 503 and constantan wire 502 around guide pegs 520a–b, 525a–b, and 530a–b, respectively.

Still referring to FIGS. 19 and 20, both wires are pulled across guide pegs 532 and 534 and then given a half twist to form junction 546. As hereinbefore described, copper wire 503 and constantan wire 502 are pulled across wire guide pegs 560a–b, and given then a half twist to form junction 547. Similarly, junctions 548, 550 and 552 are formed by performing half-twists of copper wire 503 and constantan wire 502 around guide pegs 565a–b, 570a–b, and 575a–b, respectively. Both wires are then pulled around wire guide pegs 580a–b and across wire guide pegs 585a–b, and wrapped around wire holder nail 507.

Each of these half twists is then soldered thereby making ten thermocouple junctions, namely, 506, 516, 518, 519, 517, 546, 547, 548, 550, and 552. Cut blue 11" Teflon insulated 0.015 copper lead wire 560 is then wrapped around constantan wire 502 between guide pegs 540b and 505b, and soldered thereto forming junction 508. Cut blue 9" Teflon insulated 0.015 copper lead wire 509 is similarly wrapped around constantan wire 502 between guide pegs 580b and 585b, and soldered thereto forming junction 509. Accordingly, a total of twelve junctions are formed using thermopile jig 500.

It should be clearly understood that this plurality of pegs is disposed upon thermopile jig 500 so that the resultant junctions comprising thermopile wire thread 590 will be placed in the middle of the cork strip (See FIG. 18, location 422 representing the midpoint, lateral location of junction 420, etc.) after the thermopile wire thread is threaded through the corresponding apertures in cork substrate 60, as will be hereinafter described in detail.

To complete the preparation of the composite thermopile wire thread, the excess copper and constantan portions thereof should be removed. Thus, constantan wire segment 510 disposed between guide peg 540b and junction 508 is cut therefrom first junction, and copper wire segment 511 disposed between guide peg 505a and junction 506 is cut therefrom. Following this routine, all alternating excess constantan and copper wire is cut from the corresponding junction, cutting as close as possible thereto, until all excess wire is removed. The result is the production of an alternating bimetallic wire with copper on both ends, forming a twelve-junction thermopile, with only about 5 minutes labor consumed per thermopile, a considerable savings visa vis the conventional methods used in the prior art.

Figure 21:
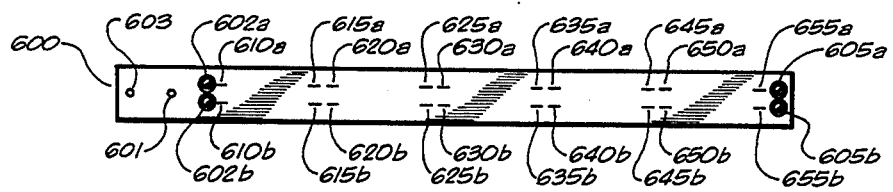
FIG. 21 is a top view depicting a thermocouple wiring board for constructing constantan-copper wire in accordance with the present invention.
Figure 22:
FIG. 22 is a front view of the wiring board depicted in FIG. 21.

In the next step and referring to FIGS. 21 and 22, composite wire for threading thermocouples disposed upon thermopile 70 is prepared using jig 600. Starting with wire holder nail 601, constantan wire is wrapped tightly around guide pegs 602a, 605a, 605b and 602b, finishing the loop at wire holder nail 603. Twenty Teflon insulated copper lead wires 9" long are then cut and stripped. Two of these copper wire leads are twisted on the constantan wire loop for each differential thermocouple pair marked on the template using two full twists. In particular, two of the 9" copper leads are double-twisted at marked template locations 610a–b, 615a–b, 620a–b, 625a–b, 630a–b, 635a–b, 640a–b, 645a–b, 650a–b, and 655a–b. Solder is then applied at each of these ten pair of junctions.

To complete the preparation of the composite thermocouple wire thread, the excess constantan should be cut away from between each successive pair of junctions. It should be understood that thermocouple jig 600 is marked with the ten thermocouple pairs such that the distance between successive thermocouples corresponds to the junction in the cork substrate in the positions for sensing A-$H_a$ and B-$H_b$.

Figure 18:
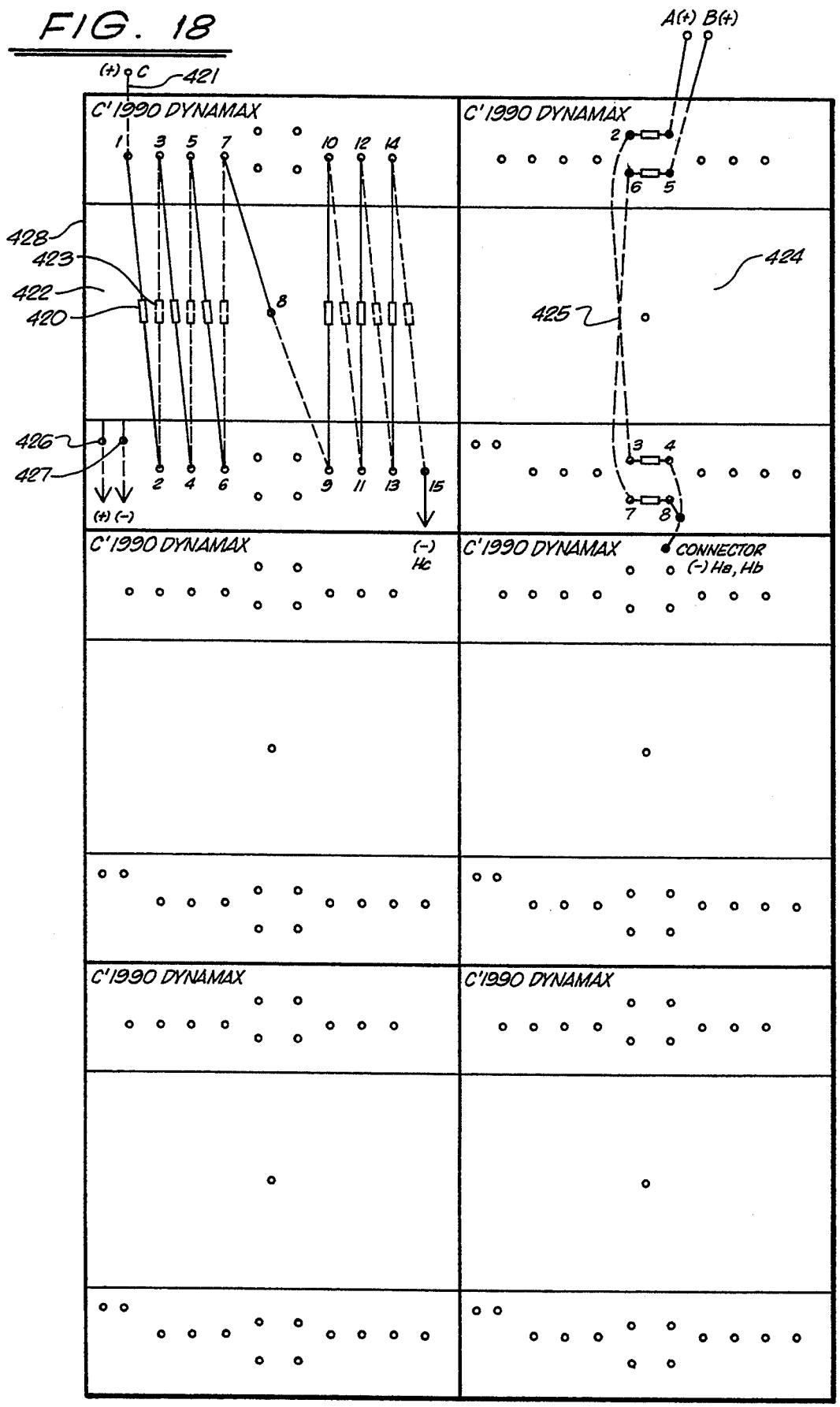
FIG. 18 depicts a cork substrate threaded with constantan-copper wire in accordance with the present invention.

Once the thermopile and thermocouple wire threads have been prepared, the next step is to thread the cork substrate. The pre-drilled cork substrate is cut apart from prepared sheets as hereinbefore described. Referring to FIG. 18, starting from the outside with lead wire 421, the entire thermopile wire is fed through hole-1 until the first junction 420 rests in the middle of the heater area on the inside, 422. Then proceed to the next hole-2, pulling the thermopile wire through again until the next junction rests in position 423 on the outside of the ensemble. The wire is fed through each hole in turn from hole-3 through hole-15 until all junctions are in position alternating between the inside and the outside. The final lead wire exits from hole-15 and becomes the $H_c$ (−) lead at the connector.

Next, each thermopile junction should preferably be sanded smooth on the inside where it touches the heater to prevent penetration, thereby removing burrs.

As shown in upper right portion of FIG. 18, on a separate substrate 424, the A-$H_a$ thermocouple is threaded into position in order of holes 1, 2, 3, and 4. The B-$H_b$ thermocouple is threaded into position in order of holes 5, 6, 7, and 8. The thermocouple wires crossing on the outside 425 fit into the gap created by the copper thermopile wire situated between hole-7 and hole-8 on the inside. It is advantageous at this step to check for shorts. Next, a strip of Kapton tape is taped over B-$H_b$ constantan wire and under A-$H_a$ constantan wire to maintain the separation therebetween.

Then, the thermocouples depicted in the upper right portion of FIG. 18 are aligned and straighten, and the holes thereof are glued with E-6000 to maintain their position. The thermopile junctions are glued into position to prevent movement.

Spray flexible acrylic circuit sealer on both sides of cork, using Vi-Crel for example, so that the cork does not absorb moisture.

Next, thread the heater wires prepared etched previously into holes 426 and 427. Spread E-6000 evenly on the heater area, and glue heater into place. Then check the heater to center it. Wrap entire assembly around a dowel and use three rubber bands to secure the heater assembly to the dowel to prevent movement while drying. Check heater after 15 min to remove excess glue and then let the glue cure overnight.

The next step is to glue the heater assembly into the insulated housing. Remove the rubber bands, but leave assembly mounted on dowel. Spread E-6000 on outside of heater assembly, center it in he insulation collar, and align the cork edge 428 with the vertical slit. It is advantageous to place a small piece of wax paper in the slit to prevent "lips" from sticking together during the curing process. Check alignment and for excess glue, then close Velcro hook straps and let set overnight. Using a sharp blade poke five holes through the loop Velcro opposite each set of wires $H_c$, C(+), A & B (a pair), $H_a$ & $H_b$ (−reference pair), V(+) & V(−) (heater pair), on the outside of the insulation housing and using tweezers, pull the wires through the insulation. Close Velcro over wires and form leads in a group, preferably at least 3" below the edge of the insulation.

Place 2½" length of ⅜" diameter conventional heat shrinkable tubing over wires. Then solder the female plug as hereinafter described. Cut all lead wires to the same length below insulation. Strip and tin all leads. Twist all three H leads together, $H_a$, $H_b$, $H_c$ and solder to the middle terminal of socket, H (See FIG. 2). All H leads are identified by exiting from the bottom of the housing 10.

Next, solder remaining leads to socket according to the following: A lead goes to A; B lead goes to B; C lead goes to C; +$V_{in}$ heater goes to D; −$V_{in}$ goes to E. Identify the B lead with an Ohm Meter between the B thermocouple and the socket end of the lead wire. The lowest resistance (about 0.2 Ohms) signifies a correct identification. The remaining wire is the "A" lead of the upper thermocouple. Either of the red heater wires can be chosen as the plus lead.

Referring to FIG. 9, extension cables should be made. Using low noise, low capacitance cables such as Belden 9931, attach cable leads to male connector as shown therein. Attach each gauge in turn to the male connector.

Next, test each gauge with power applied to the heater according to the specifications using the dowel as a dummy plant, and logging the data for five to 10 minutes from the four signals shown in FIG. 9. Record the information and check for correct sign and magnitude of the signals. Move the dowel up ½ the diameter of the dowel, and record C-$H_c$ to see if the signal drops 25 to 50% or more when the radial heat flux drops momentarily within three to five seconds. After about ½ minute, check the A-$H_a$ and B-$H_b$ signals to see if the there is and increase of 40 uV to 100 uV in each signal, indicating the higher temperatures surrounding the heated dowel from the static test are recorded on the upper thermocouple's, and a lower temperature on the lower junctions.

Next step is the final assembly, provided the test results are satisfactory. Force glue from syringe into heat shrink tubing, and using heat blower, shrink the tubing until it fits snugly around the wires. Brush Stop Arc, flexible acrylic circuit sealer diluted 50/50 with acetone, on exposed cork substrate for final moisture sealing. Glue wire holes in insulation closed with E-6000. Tuck excess lead wires exiting from the heat shrink underneath hook Velcro, and glue hook Velcro strap down on loop Velcro over the wires. Let set for two hours and then retest all gauges. Touch up painted areas and cut Aluminized PVC shields to size from Vinalum stock.

Now referring to FIGS. 23–32 there is depicted an alternative embodiment of the present invention which promotes firm contact between the heater means as has been hereinbefore described in detail, the stem section being measured and appropriate temperature sensing means, as will be hereinafter described. It will become evident to those skilled in the art that this embodiment is particularly suitable for measuring the sap flow in small diameter plants such as grains, seedlings and floricultural species. Indeed, water consumption or transpiration of small deciduous, conifers, ornamentals and nursery stock plants with diameters of 5–7 mm may be conveniently and accurately determined under a diversity of environmental conditions.

Figure 23:
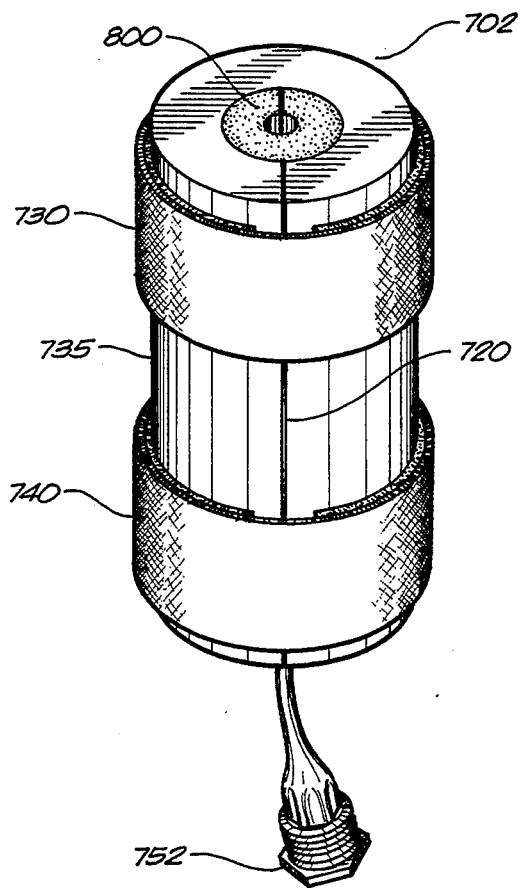
FIG. 23 is a frontal perspective view depicting an alternate embodiment of the present invention.
Figure 24:
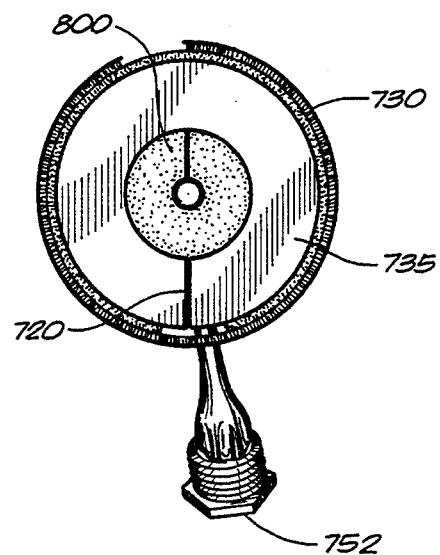
FIG. 24 is a top plan view of the embodiment depicted in FIG. 23.

For convenience, the numerals used in FIGS. 23–32 are analogous to the numerals used in corresponding FIGS. 2–8. Thus, heater 62 depicted in partial cut-away view FIG. 4 corresponds to heater 762 depicted in FIG. 26. Similarly, integrated embodiment 2 depicted in FIG. 2 corresponds to alternate 702 in FIG. 23. Referring now to FIGS. 23 and 24, there are shown frontal perspective and top plan views, respectively, depicting alternate embodiment 702 of the present invention. There is shown soft-cell collar 735 circumferentially enclosing and protecting internal substrate and concomitant electronics assembly (see FIG. 26 ) from water, solar radiation and weather intrusion. Preferably Velcro fastener straps 730 and 740 secure collar 735 about substrate 760 across gap 720 and, in turn, ultimately about the particular enclosed plant stem portion for which sap flow is being measured. Plug 752 interconnects the internal electronics assembly with suitable datalogger means. Also shown is foam collar insert 800 to further shield substrate 760 from moisture and environmental conditions.

Figure 25:
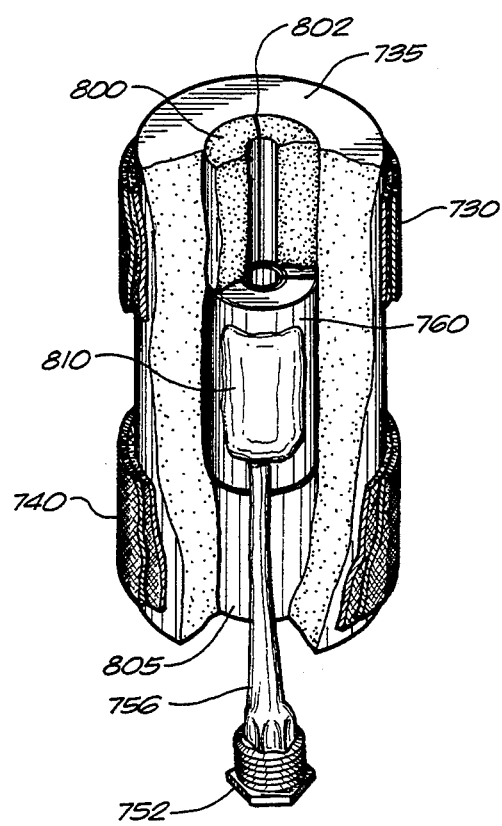
FIG. 25 is a frontal cut-away view of the embodiment depicted in FIGS. 23 and 24.
Figure 26:
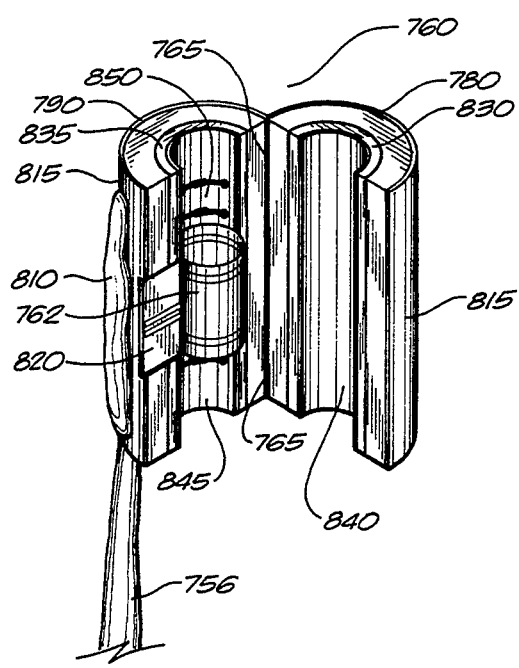
FIG. 26 is a frontal isolated view of a portion of the embodiment depicted in FIGS. 23-25, with the heater and electronic components shown.

Referring now to FIGS. 25 and 26 there is depicted frontal cut-away view of collar 735 and frontal isolated view of substrate 760, respectively. Substantially cylindrical substrate 760 is seen in a sealable relationship with collar 735 and upper and lower collar inserts 800 and 805, respectively. Collar insert 800 is constructed with slit 802 to be easily placed around the stem portion and inserted snugly within cylindrical annulus located immediately above top of substrate 760. Similarly, collar insert 805 is constructed with slit 807 (not shown) to be easily placed around the stem portion and inserted snugly within cylindrical annulus located immediately below bottom of substrate 760. Also shown is epoxy sheath 810 which preferably covers exposed wiring to prevent damage thereto from handling or abrasion.

Specifically referring to FIG. 26 there is depicted substrate 760 comprising preferably congruent portions 780 and 790 which are preferably hingedly joined on common edge 765 by Kapton sheet 815 which is glued to corresponding external convex surface of substrate portions 780 and 790. Thus, the overlap of Kapton sheet 815 across common edge 765 causes substrate portions 780 and 790 to pivot relative to each other and about edge 765 functioning as the axis of rotation. There are also seen foam layers 830 and 835 which are affixed to corresponding interior concave surface of substrate portions 780 and 790, respectively. Foam layers 830 and 835 preferably comprise double-stick foam tape, typically sold by 3M. In accordance with the present invention, gasket layers 840 and 845 are preferably attached to the other, concave side of double-stick foam tape layers 830 and 835, respectively, to protect substrate 760 from moisture accumulation and provide optimal tradeoff between strength and flexibility. Representative gasket material is that commercially available for use with automobiles and chemically treated to resist oil, gasoline and water leakage.

Still referring to FIG. 26, substrate portions 780 and 790 are preferably constructed from acrylic tubing to impart rigidity and structural integrity to integrated substrate 760 with its associated electronic components will be hereinafter described in detail. For example, substrate 760 may be constructed from Plexiglass with outside and inside diameters of ⅝" and ⅜", respectively. Thus, it has been found that an acrylic substrate having a wall thickness of about ⅛" is sufficient to accomplish the teachings of the present invention. As should be apparent to those skilled in the art, foam layers 830 and 835 provide sufficient cushioning to the electronic components contained therein. As has been hereinbefore described in detail (e.g., FIG. 4), heater 762 is contained within substrate 760. Recess or lip 820 is configured to assure that heater 762 is securely and sealably contained within substrate 760 when substrate portion 780 is pivotally received by substrate portion 790.

It is a feature and distinct advantage of the embodiment depicted in FIGS. 23–26, that heater 762 and related electronic components 850 are exclusively contained within substrate portion 790. Thus, as clearly shown in FIG. 26, the preferred clam-shell construction manifest by the pivotal joinder of substrate portion 780 with substrate portion 790, and enclosure thereof within collar 735 and coupled with supplemental protection afforded by collar inserts 800 and 805, provide a secure and weather and radiation protected means for measuring sap flow in plants and the like, heretofore unknown in the art.

Figure 27:
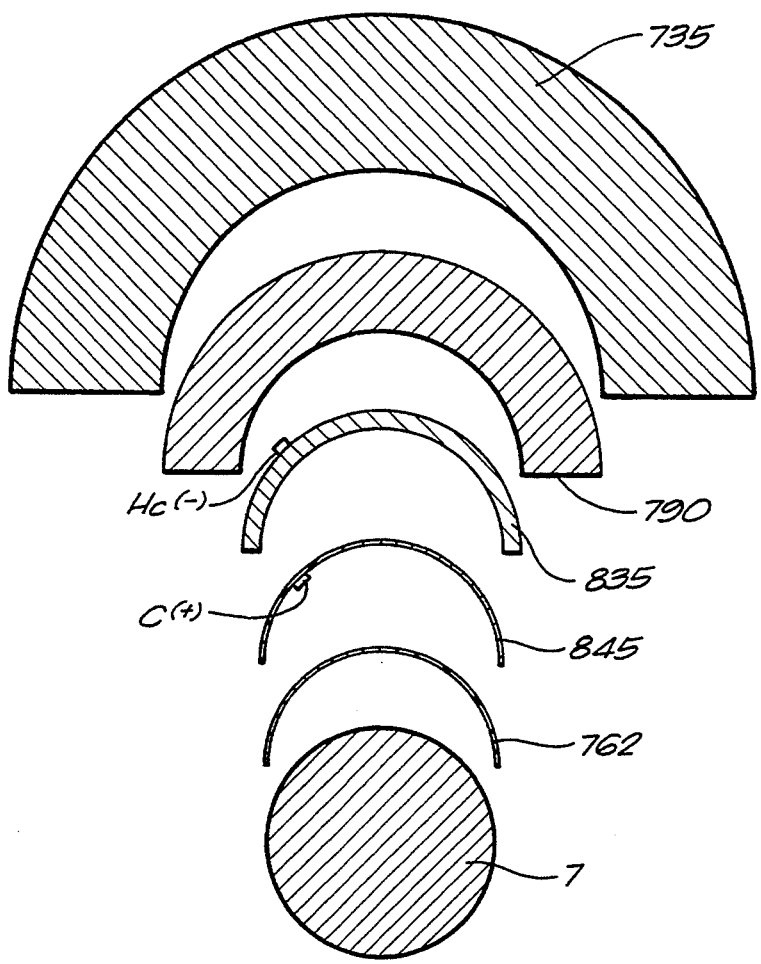
FIG. 27 is an exploded frontal view of the components comprising the portion of the embodiment depicted in FIG. 26.

Referring to FIG. 27, there is depicted an exploded frontal view of the components comprising the instant alternative embodiment of the present invention showing each of the layers, from the outermost foam insulating collar 735 to innermost stem portion 7. Thus, successive layers depicted are, from outer to inner layer, collar 735, substrate portion 790, foam tape layer 835, gasket layer 845, heater strip 762 and stem region 7. Depicted on foam tape layer 835 is a negative or cold connection and on gasket layer 845 is a positive or hot junction.

Figure 28:
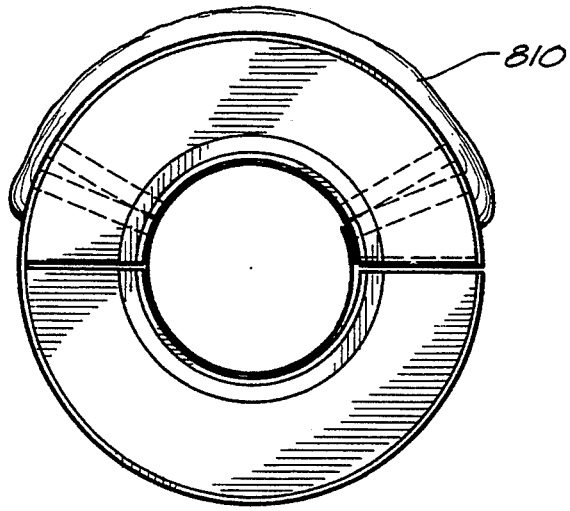
FIG. 28 is a top plan view of the components depicted in FIG. 27 in exploded form.

While depicted in FIGS. 26–28 with substantially a circular cross-section, it should be clearly understood that it is within the teachings of the present invention that embodiments may be configured with an elongated or elliptical cross-section. Indeed, it has been discovered that a sap flow device having an elliptical cross-section frequently better accommodates stems than such a device having a circular cross-section. This seems to be particularly true for small stem plants or for stems of grasses, wheat, millet, etc.

Figure 29:
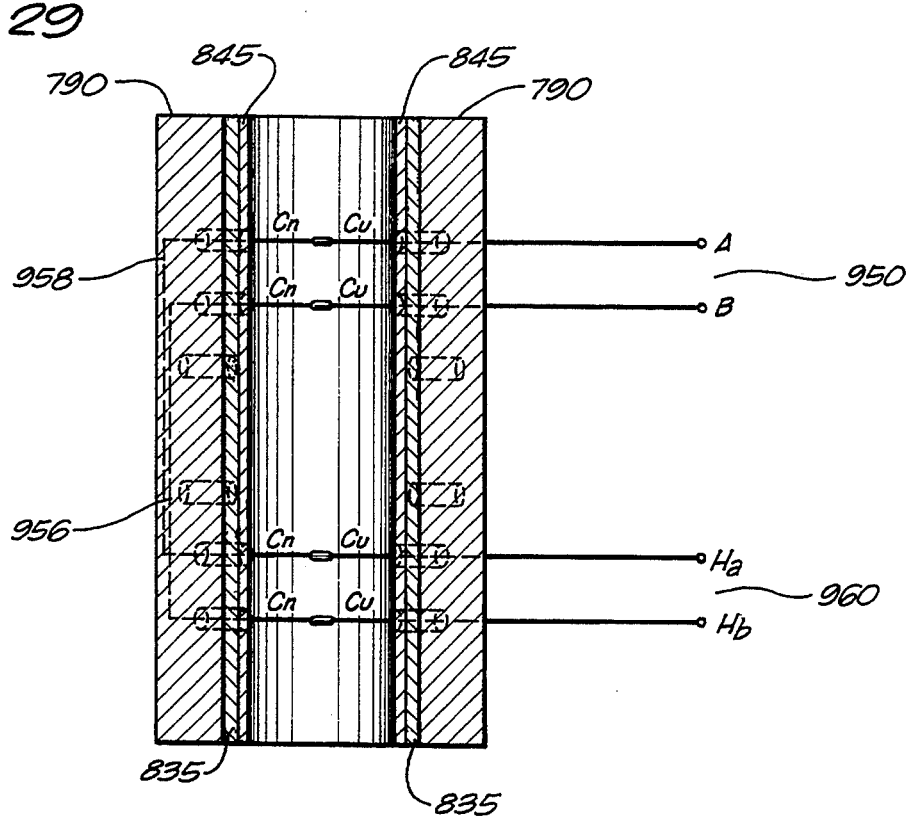
FIG. 29 is a simplified cut-away front view of the alternate embodiment of the present invention depicted in FIGS. 23-28, depicting electrical components thereof.
Figure 30:
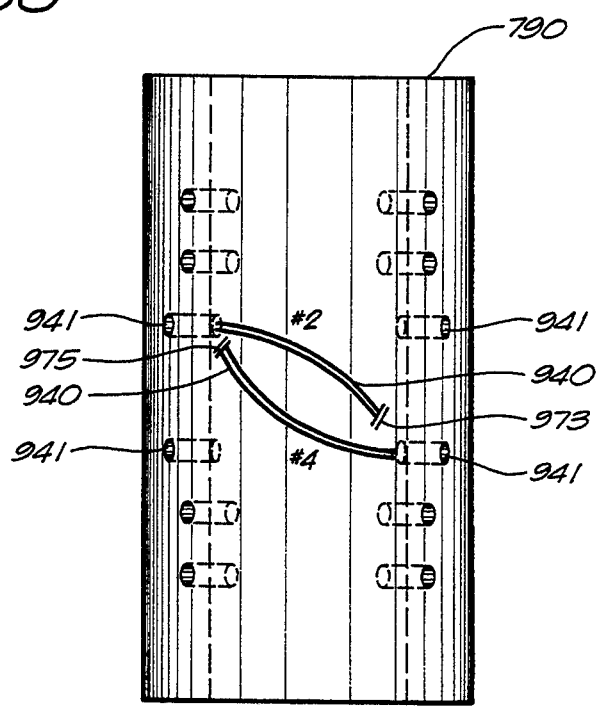
FIG. 30 is a front view of the electrical wiring embodying a thermopile in accordance with the alternate embodiment of the present invention depicted in FIGS. 23-28.
Figure 31:
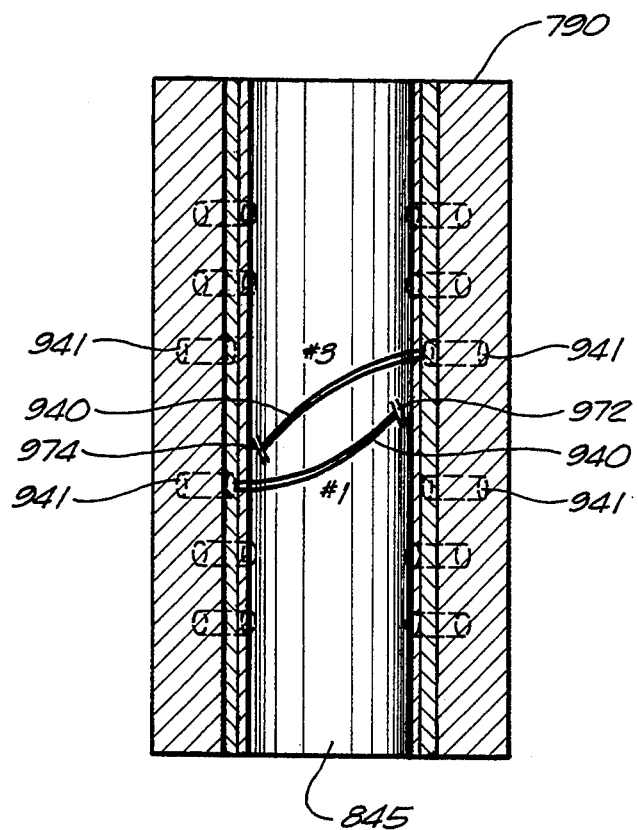
FIG. 31 is a rear view of the embodiment depicted in FIG. 30.
Figure 32:
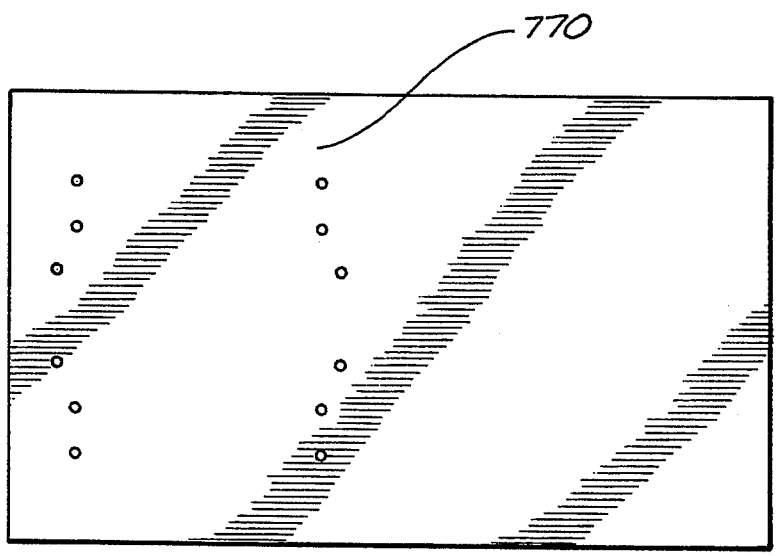
FIG. 32 depicts a rigid substrate showing a wiring template configured in accordance with the alternate embodiment of the present invention depicted in FIGS. 23-31.

Now referring to FIGS. 29–32, there is shown the preferred configuration for incorporating heating means 762 and the temperature sensing means of the present invention entirely into only one portion 790 of substrate 760. In particular, FIG. 32 shows drilling template 770 that should preferably be drilled into rigid acrylic substrate portion 790, for receiving thermopile 940 and copper-constantan thermocouple pairs 950 and 960 as depicted in FIGS. 29–31. The use of such a template allows self-alignment of the position of the thermocouples and the like in substrate portion 790. Not only does this approach engender consistent performance, but also improves manufacturing reliability.

Of course, it should be evident to those skilled in the art, that as another alternative embodiment of the present invention the temperature sensing means may be manifest as a trace contained upon a flexible circuit board instead of composite wiring and the like. Such a flexible circuit board would comprise a multilayer laminate as is conventional in the semiconductor art. Such an embodiment would facilitate further miniaturization of sap flow gauges implemented according to the teachings of the present invention, and would promote its portability and reusability aspects.

FIG. 29, similar to FIGS. 5 and 10, depicts two pair of differential thermocouples 950 and 960, which provide two signals indicating the temperature gradient above and below heater 762 (not shown) and concurrently measure the conducted stem heat transfer. Again, similar to FIGS. 7 and 8, depicting thermopile 70 comprising a plurality of copper-constantan thermocouples connected in series, FIG. 30 shows thermopile 940 with illustrative copper-constantan junctions 972, 973, 974 and 975.

FIGS. 30 and 31 show corresponding front and rear views of electrical wiring threading sequence (numbered #1, #2, #3, #4) through holes or vias 941 embodying a thermopile in accordance with this alternate embodiment of the present invention. Thus, segments of each of copper wire and constantan wire is alternately fed through holes 941 in template 770. As shown, #2 and #4 junctions are inserted into appropriate holes in substrate 790 and jointly twisted into position on the inside of substrate 790. Then junctions #1 and #3 are twisted into position on inside of gasket layer 845 of substrate portion 790.

In accordance with the teachings of the present invention, it has been discovered that using a rigid outer shell or housing for a sap flow gage provides a more durable measuring device than has been hereinbefore known in the prior art. In addition, such a device is easier to install. The instant clam-shell design with its concomitant foam and rubber gasket layers promote firm contact between its heater and thermocouples and the stem. As has been described, this alternative embodiment of the present invention is particularly suitable and reliable for small diameter plants and the like. The preferred Kapton hinge provides excellent hinge-strength and adequate longevity for repetitive application of the present invention in the field.

It is also a significant feature of the present invention that its flexible core is inherently designed to conform to stem irregularities and also to accommodate growth and diurnal shrinkage and swelling. Since the present invention adapts to stems and the like of non-circular cross-section, it promotes maximal contact between the stem and all electronic sense points and the heater.

It should be understood by those skilled in the art that to incorporate the temperature sensing devices used by the present invention into substrate portion 790 and accomplish the objectives thereof, requires a novel configuration of thermocouples. Thus, instead of the zig-zag pattern having twelve junctions depicted in FIGS. 7–8 and hereinbefore discussed in detail, the alternative embodiment depicted in FIGS. 29–31 has only four junctions. In addition, these four junctions are not configured in a zig-zag pattern but are configured to be disposed about the circumference of foam layer 835 of substrate portion 790 and inside of gasket layer 845, i.e., to be disposed adjacent heater 762. Indeed, as should be clear to those skilled in the art, this configuration inherently uses the entire length of copper wire affixed to substrate 790 as a heat sensing means. Ergo, in effect, the thermal conductivity of copper wire has been advantageously exploited by its being situated circumferentially of heater 762 and inside concave surface of foam layer 835 of substrate portion 790. As a consequence, in accordance with the teachings of the present invention, temperature is being measured throughout the substrate's circumference, thereby measuring only heat transfer by radial conduction of substrate portions 780 and 790 through the core.

As will be appreciated by those skilled in the art, it has also been discovered that by reducing the diameter of wire used from about 0.010" to 0.005", in conjunction with the other novel design features manifest in the present invention, the thermopile signal strength has been essentially doubled, having increased from 50 to 100 $\mu$V under normal power and operating at zero flow conditions. As will also be appreciated by those skilled in the art, such improved performance is a prerequisite for reliably measuring sap flow at a low flow rate.

Figure 33:
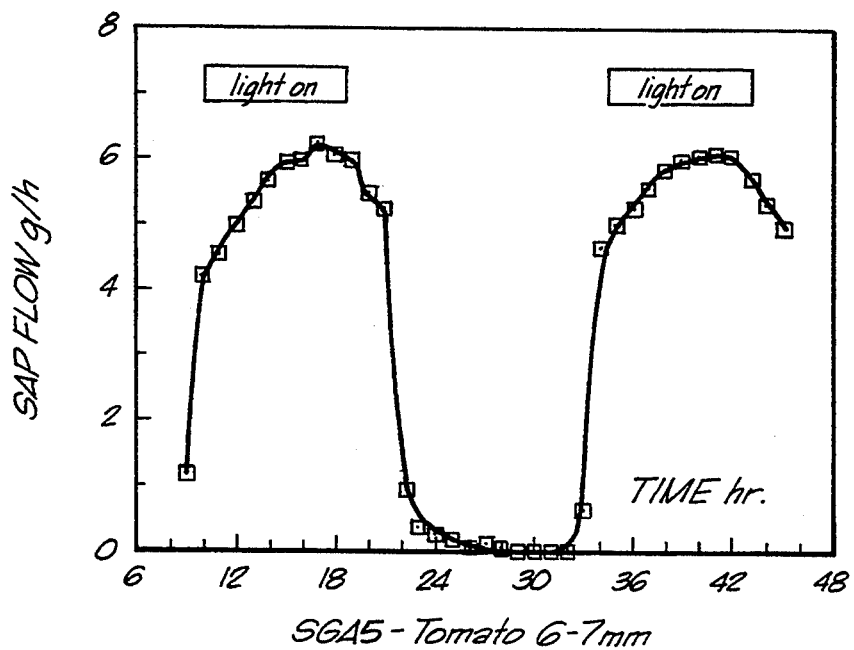
FIG. 33 depicts a plot of sap flow vs. time in a tomato stem.
Figure 34:
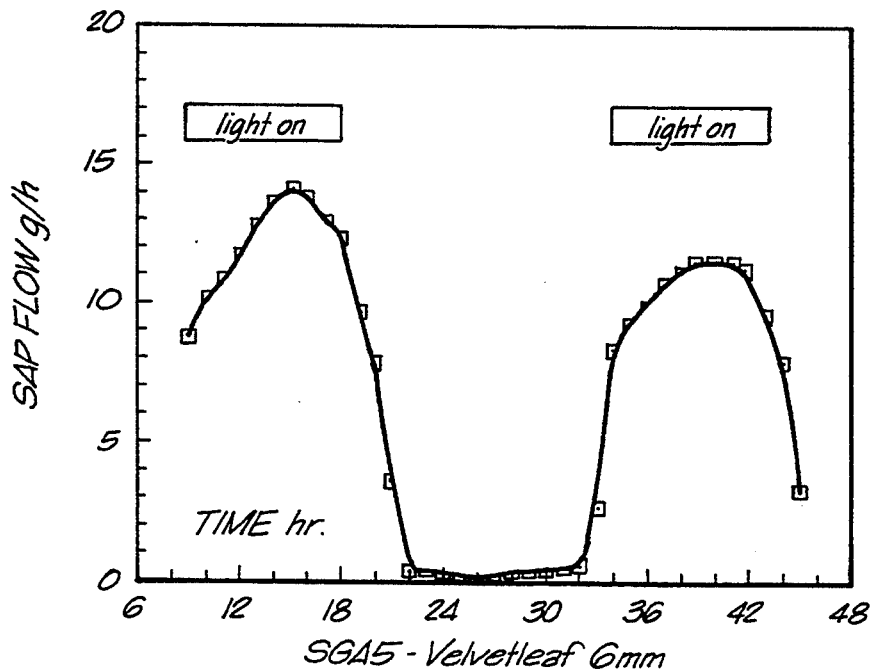
FIG. 34 depicts a plot of sap flow vs. time in a velvetleaf stem.
Figure 35:
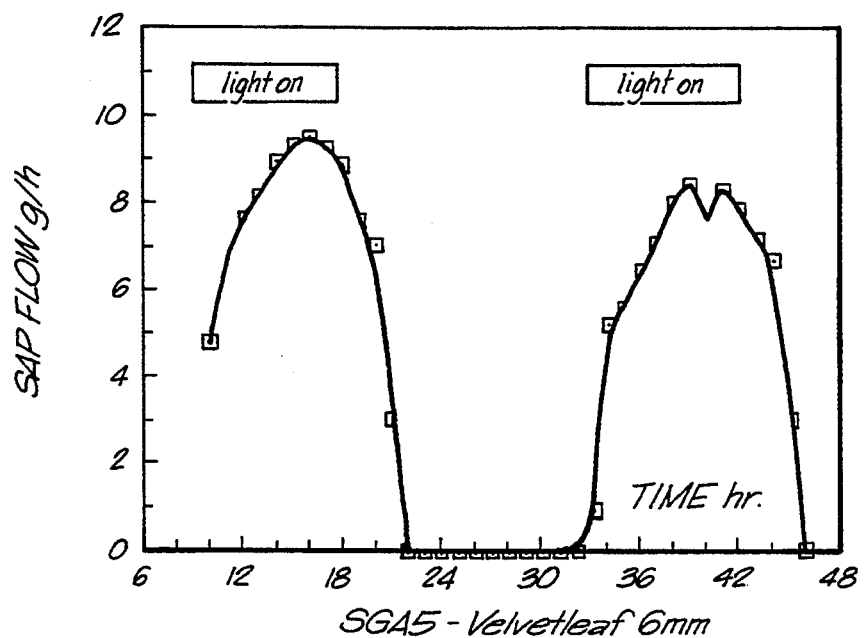
FIG. 35 depicts another plot of sap flow vs. time in a velvetleaf stem.
Figure 36:
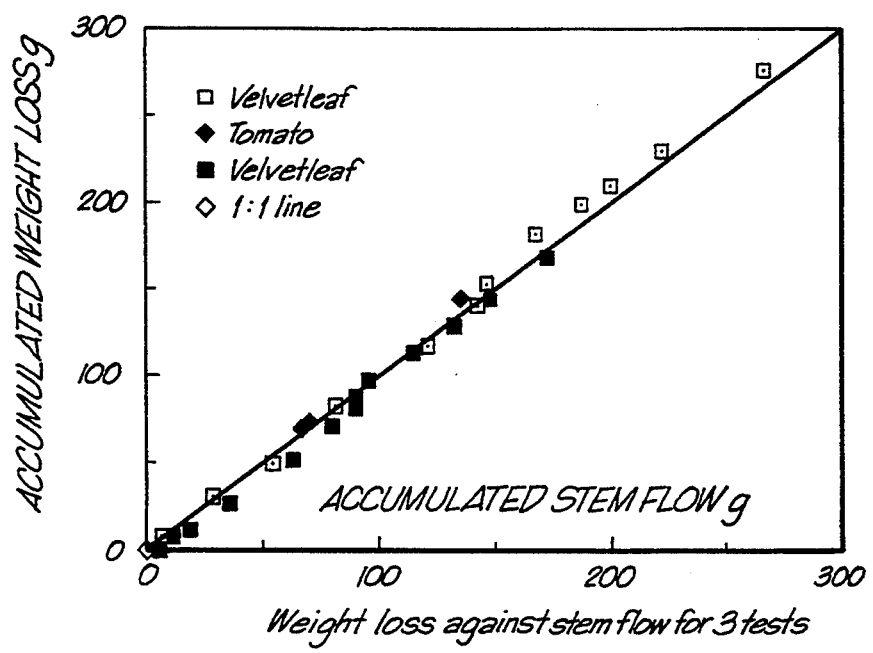
FIG. 36 depicts a composite plot of cumulative sap flow and weight loss corresponding to the plots depicted in FIGS. 33-35.

An example of such an embodiment of the present invention is identified as the SGA5 Dynagage. FIGS. 33–36 illustrate test results obtained with two such embodiments, 5 mm sap flow gauges. FIGS. 33–35 depict plots of sap flow vs. time of day and FIG. 36 depicts a composite plot of cumulative sap flow and weight loss in the three tests depicted. One 5 mm Dynagage was applied to a velvetleaf plant, specifically known as *Arbutilun theophrasti*, representing a common weed; the other 5 mm Dynagage was applied to a young tomato plant, specifically known as *Lycopersicum esculentum*. Tests were performed in a well-insulated, windowless, and unheated storage room under a single 400 watt metal halide lamp, providing a light level of about 17% of maximal daylight at the top of the plants, for 12 or 14 hours per day. Air temperature varied from 12°–25° C., indicative of normal outside conditions during late Fall and Winter, and heating provided by the lamp. These plants were growing in 1 liter metal containers filled with potting soil and amply supplied with water. Evaporation was minimized by a cover of cellular plastic on the substrate surface; the average loss due to evaporation was determined at about 0.5 g/hr by a separate measurement.

The first day and night of each test were used to establish the value of $K_{sh}$ prior to the time that the light was turned on, early in the morning. This value was calculated assuming zero sap flow during the early morning hours in darkness, and differed little between the two gauges, averaging about 0.30 watts/millivolt. The power level of these gauges was about 0.074 watts, at 4 volts DC input to each of respective heater. As will be appreciated by those skilled in the art, this heating rate appears to be acceptable, producing a maximum heating of the sap by about 3.0° C. as measured by the temperature difference of the stem above and below the heater.

Each test was conducted during a two-day period. The corresponding hourly sap flow rates are shown in FIGS. 33-35. In all cases, the transpiration responds quickly to the onset of light, then increases gradually to a late afternoon maximum and declines thereafter, to drop precipitously as the light was extinguished. The daytime variation is caused by the rise and fall of the ambient temperature and the associated vapor pressure deficit between the leaves and the surrounding air. Data collected was surprisingly free of spurious noise. The maximum sap flow rate of the tomato plant was about 6 gram/hr; the maximum sap flow rate of the velvetleaf plant was about 14 gram/hr and 9.5 gram/hr, in the two tests. As should be evident to those skilled in the art, the lower sap flow rate in the second test was attributable to lower ambient temperatures. During the periods that the highest sap flow rate was recorded, the sap heating, i.e., dT, was about 2° C. Thus, flow rates as high as 50 gram/hr could accurately be measured with the present invention. The following tabulation per test of the weight record clearly demonstrates the correlation between total weight loss and total sap flow throughout the test period. There is a deviation of only from −7 to +2% between total weight loss and total sap flow.

| Plant | Total Sap Flow (gms) | Total Weight Loss (gms) | Dev. |
| --- | --- | --- | --- |
| Tomato | 136.1 | 146 | −7% |
| Velvetleaf | 267.3 | 276 | −3% |
| Velvetleaf | 173.3 | 169 | +2% |

Accordingly, the present invention provides embodiments of a sap flow gauge heretofore unknown in the art. The present invention teaches a portable and reusable synergistic clam-shell construction in conjunction with inherent cushioning of its uniquely configured internal electronic components preferably in a layered substrate affixed to one portion of the shell. With its unique thermopile design, the present invention enables accurate and reliable determination of sap flow in trees and plants. As has been described in detail, these advantageous results are determined using measurement of radial conductive heat loss, axial conductive heat loss, and sap temperature increase as the sap emerges from the heated stem region. Unlike, the Detectif device, the present invention accommodates stem irregular shapes and other changes thereto, and provides absolute sap flow rate. Unlike the Kitano and other prior art fluid flow devices cited, the present invention provides a four-channel approach to measuring sap flow rate, and advantageously seals its substrate of electronic components from water, solar radiation and weather intrusion.

Other variations and modifications will, of course, become apparent from a consideration of the features hereinbefore described and depicted. Accordingly, it should be clearly understood that the present invention is not intended to be limited by the particular features hereinbefore described and depicted in the accompanying drawings, but that the concept of the present invention is to be measured by the scope of the claims herein.

What is claimed is:

1. In a system for measuring sap flow in a stem region of a plant, under diverse environments, a portable flow sensor comprising:

a rigid clam-shell housing comprising a first portion and a second portion, said first and second portions obtained by completely cutting said housing along its longitudinal axis;

said first portion and said second portion of said housing pivotally interconnected at a corresponding longitudinal edge to form a joinder thereof;

said joinder of said first portion and said second portion of said housing disposed abuttably of said stem region and configured to be adjustably and concentrically received by said stem region, without invading any surface thereof;

a first flexible substrate fixedly attached to said first portion of said housing and disposed annularly and abuttably inside of said first portion and including a first temperature sensing means imbedded thereon;

a second flexible substrate fixedly attached to said second portion of said housing and disposed annularly and abuttably inside of said second portion;

a collar member configured to be sealably disposed circumferentially of said housing, for securing said housing to said stem region for preventing invasion by water and for shielding from radiation;

said first temperature sensing means generating a first signal responsive to radial temperature difference between interior and exterior surface layers of said first substrate, for measuring ambient heat loss;

a heater means disposed annularly of said interior surface of said first substrate and fixedly attached thereto;

a sensing cable interconnected with said heater means for generating a second signal responsive to power input thereto;

a first differential temperature sensing pair, comprising a second temperature sensing means and a third temperature sensing means, disposed immediately above said heater means and having said second temperature sensing means disposed a first distance above said third temperature sensing means;

a second differential temperature sensing pair, comprising a fourth temperature sensing means and a fifth temperature sensing means, disposed immediately below said heater means and having a fourth temperature sensing means disposed a second distance above said fifth temperature sensing means;

said second temperature sensing means interconnected with said fourth temperature sensing means to generate a third signal responsive to temperature gradient of said sap flow in said stem region and responsive to axial heat loss by conduction through said stem region;

said third temperature sensing means interconnected with said fifth temperature sensing means to generate a fourth signal also responsive to said temperature gradient of said sap flow in said stem region and responsive to axial heat loss by conduction through said stem region; and a means for transmitting said four signals to datalogger means, for determining said sap flow.

2. The apparatus recited in claim 1 wherein said first flexible substrate is a composite comprised of a bottom foam layer and a top gasket layer.

3. The apparatus recited in claim 1 wherein said second flexible substrate is a composite comprised of a bottom foam layer and a top gasket layer.

4. The apparatus recited in claim 1 wherein said first distance and said second distance are equal.

5. The apparatus recited in claim 1 wherein said substrate includes a plurality of apertures configured for receiving a conducting wire therethrough.

6. The apparatus recited in claim 5 wherein said conducting wire comprises alternating strands of copper and constantan soldered together at each junction thereof.

7. The apparatus recited in claim 1 wherein said first temperature sensing means comprises a series of a plurality junctions disposed circumferentially of said first substrate portion and adjacent said heater means.

8. The apparatus recited in claim 1 wherein said collar member comprises a body portion and a pair of collar inserts, comprising a first collar insert and a second collar insert, each said first and second collar insert configured to be sealably received by an annulus formed on its exterior by said body portion of said collar member and formed on its interior by said housing, respectively.

9. The apparatus recited in claim 1 wherein said first and said second flexible substrates, said first temperature sensing means, said first differential temperature sensing pair, said second differential temperature sensing pair and said heater means are contained on a flexible circuit board.

10. In a system for measuring sap flow in a stem region of a plant, under diverse environments, a portable flow sensor comprising:

a rigid clam-shell housing comprising a first portion and a second portion, said first and second portions obtained by completely cutting said housing along its longitudinal axis;

said first portion and said second portion of said housing pivotally interconnected at a corresponding longitudinal edge to form a joinder thereof;

said joinder of said first portion and said second portion of said housing disposed abuttably of said stem region and configured to be adjustably and concentrically received by said stem region, without invading any surface thereof;

a first flexible substrate fixedly attached to said first portion of said housing and disposed annularly and abuttably inside of said first portion and including a thermopile imbedded thereon;

a second flexible substrate fixedly attached to said second portion of said housing and disposed annularly and abuttably inside of said second portion;

a collar member configured to be sealably disposed circumferentially of said housing, for securing said housing to said stem region for preventing invasion by water and for shielding from radiation;

said thermopile generating a first signal responsive to radial temperature difference between interior and exterior surface layers of said first substrate, for measuring ambient heat loss;

a heater means disposed annularly of said interior surface of said first substrate and fixedly attached thereto;

a sensing cable interconnected with said heater means for generating a second signal responsive to power input thereto;

a first differential thermocouple pair, comprising a first thermocouple and a second thermocouple, disposed immediately above said heater means and having said first thermocouple disposed a first distance above said second thermocouple;

a second differential thermocouple pair, comprising a third thermocouple and a fourth thermocouple, disposed immediately below said heater means and having a third thermocouple disposed a second distance above said fourth thermocouple;

said first thermocouple interconnected with said third thermocouple to generate a third signal responsive to temperature gradient of said sap flow in said stem region and responsive to axial heat loss by conduction through said stem region;

said second thermocouple interconnected with said fourth thermocouple to generate a fourth signal also responsive to said temperature gradient of said sap flow in said stem region and responsive to axial heat loss by conduction through said stem region; and a means for transmitting said four signals to datalogger means, for determining said sap flow.

11. The apparatus recited in claim 10 wherein said first flexible substrate is a composite comprised of a bottom foam layer and a top gasket layer.

12. The apparatus recited in claim 10 wherein said second flexible substrate is a composite comprised of a bottom foam layer and a top gasket layer.

13. The apparatus recited in claim 10 wherein said first distance and said second distance are equal.

14. The apparatus recited in claim 10 wherein said substrate includes a plurality of apertures configured for receiving a conducting wire therethrough.

15. The apparatus recited in claim 14 wherein said conducting wire comprises alternating strands of copper and constantan soldered together at each junction thereof.

16. The apparatus recited in claim 10 wherein said thermopile comprises a series of a plurality junctions disposed circumferentially of said first substrate portion and adjacent said heater means.

17. The apparatus recited in claim 10 wherein said collar member comprises a body portion and a pair of collar inserts, comprising a first collar insert and a second collar insert, each said first and second collar insert configured to be sealably received by an annulus formed on its exterior by said body portion of said collar member and formed on its interior by said housing, respectively.

18. The apparatus recited in claim 10 wherein said first and said second flexible substrates, said thermopile, said first differential thermocouple pair, said second differential thermocouple pair and said heater means are contained on a flexible circuit board.

* * * * *